United States Patent
Danilov et al.

(10) Patent No.: US 12,359,913 B2
(45) Date of Patent: Jul. 15, 2025

(54) METHOD FOR DETERMINING THE GEOMETRY OF A DEFECT AND FOR DETERMINING A LOAD LIMIT

(71) Applicant: ROSEN SWISS AG, Stans (CH)

(72) Inventors: Andrey Danilov, Stans (CH); Matthias Peussner, Westerkappeln (DE)

(73) Assignee: Rosen IP AG, Stans (CH)

( * ) Notice: Subject to any disclaimer, the term of this patent is extended or adjusted under 35 U.S.C. 154(b) by 145 days.

(21) Appl. No.: 17/602,939

(22) PCT Filed: Apr. 9, 2020

(86) PCT No.: PCT/EP2020/060190
§ 371 (c)(1),
(2) Date: Oct. 11, 2021

(87) PCT Pub. No.: WO2020/208156
PCT Pub. Date: Oct. 15, 2020

(65) Prior Publication Data
US 2022/0163325 A1    May 26, 2022

(30) Foreign Application Priority Data

Apr. 9, 2019    (EP) .................................. 19168279
Apr. 10, 2019   (EP) .................................. 19168530

(51) Int. Cl.
*G01B 21/20*    (2006.01)
*G01N 33/2045*  (2019.01)

(52) U.S. Cl.
CPC ......... *G01B 21/20* (2013.01); *G01N 33/2045* (2019.01)

(58) Field of Classification Search
None
See application file for complete search history.

(56) References Cited

U.S. PATENT DOCUMENTS

| | | | |
|---|---|---|---|
| 6,085,528 A * | 7/2000 | Woodall | F17D 1/04 62/53.2 |
| 6,203,631 B1 * | 3/2001 | Bowen | B60K 15/03006 420/92 |
| 2010/0005864 A1 * | 1/2010 | Minnaar | G01N 3/20 73/49.1 |
| 2010/0042379 A1 * | 2/2010 | Minnaar | G06F 30/23 703/2 |
| 2011/0167914 A1 * | 7/2011 | Sutherland | G01N 27/902 73/643 |
| 2014/0336806 A1 * | 11/2014 | Bewlay | G06F 30/00 700/98 |
| 2016/0034422 A1 * | 2/2016 | Brandt | G01N 29/4436 708/424 |
| 2017/0191361 A1 | 7/2017 | Khalaj Amineh et al. | |
| 2017/0326629 A1 * | 11/2017 | Lorentzen | G01N 21/8914 |
| 2018/0045680 A1 * | 2/2018 | Thompson | G01N 29/2412 |
| 2018/0196005 A1 * | 7/2018 | Fanini | E21B 47/007 |

FOREIGN PATENT DOCUMENTS

EP    3467489 A1    4/2019

* cited by examiner

*Primary Examiner* — Shelby A Turner
*Assistant Examiner* — Brandon J Becker
(74) *Attorney, Agent, or Firm* — Husch Blackwell LLP

(57) ABSTRACT

A method is provided for determining the geometry of one or more real, examined defects of a metallic and in particular magnetizable object, in particular a pipe or a tank, by means of at least two reference data sets of the object generated on the basis of different, non-destructive measuring methods.

21 Claims, 18 Drawing Sheets

METHOD FOR DETERMINING THE GEOMETRY OF A DEFECT AND FOR DETERMINING A LOAD LIMIT

CROSS REFERENCE

This application claims priority to PCT Application No. PCT/EP2020/060190, Apr. 4, 2020, which itself claims priority to EP Application Nos. 19 168 530.4 and 19 168 279.8, filed Apr. 10, 2019 and Apr. 9, 2019, respectively, the entirety of all of which are hereby incorporated by reference.

FIELD OF THE INVENTION

The present invention relates to a method for determining the geometry of a defect as well as a method for determining a load limit of an object which is under pressure at least during operation.

BACKGROUND

One of the essential tasks of pipeline inspections, especially with so-called intelligent pigs, is the prediction of safe operating conditions which result from the condition of the pipeline. Pipeline operators are particularly interested in the condition of any weld seams and the number and size of defects. Defects are, for example, areas with metal losses due to corrosion, cracks, or other weaknesses in a wall of an object provided in particular for the storage or transport of liquid or gaseous media. These include, for example, pipes, pipelines, or tanks.

Knowledge of the maximum pressure ("burst pressure") applicable to a pipeline, from which the pipeline is destroyed, is relevant for the operating pressures that can be set in the pipeline. The burst pressure is used for the quantitative determination of the load limit. Accordingly, accurate prediction of this pressure is important. Currently, a defect is only approximated with regard to its length, width and depth and is therefore regarded as a box for the calculation of this limit value. However, this conservative approach is disadvantageous for both metal losses due to corrosion and cracks, both on the outside or inside of a pipeline, since the simplified geometric figures necessarily overestimate the current structure of the defect. This leads to underestimation of the burst pressure of the object and thus to an underestimation of the permitted operating pressures. An object that can be operated at a higher pressure, such as an oil pipeline or a gas tank, can, however, be operated much more economically.

The measuring methods that take into account the magnetic flux leakage density (MFL measuring methods or MFL methods) are preferably used to find defects due to corrosion. Other methods, in particular methods using ultrasound, are used for the detection of cracks on the inside or outside of an object. These non-destructive measuring methods include electromagnetic-acoustic methods (EMAT methods or EMAT measuring methods) in which, due to eddy current-induced magnetic fields, sound waves, in particular in the form of guided waves, are generated in the wall of the object to be examined, as well as methods introducing ultrasound directly into the object wall, hereinafter referred to as ultrasonic methods (UT methods or UT measuring methods). In the prior art, near-surface, particularly smaller cracks are also searched for using eddy current measuring methods, hereinafter referred to as EC methods or EC measuring methods.

It is state of the art for measuring the corrosion of an object to have scans of magnetic flux leakage data (MFL data) based on magnetic flux leakage measurements (MFL measurements) evaluated by specially trained people to determine the size of the (corrosion) defects. The same applies to the evaluation of measurement data obtained on the basis of EMAT, UT and EC measuring methods. The signals displayed in the scans are parameterized and evaluated in boxes. The assumptions necessary for this evaluation of the measurement results, also known as sizing, are on the one hand proprietary. On the other hand, the interpretation of the measurement results is strongly influenced by the experience of the evaluators. Ultimately, the quality of the forecasts can only be ensured by examining the pipeline on site. Particularly in the case of excavations, this is associated with high costs for the operator. The most widespread industry standard API 1163 describes the disadvantageous effects of the evaluation approach described above. It is well documented that the quality of this approach depends heavily on the knowledge of the viewer. The approaches carried out in practice are always an interpretation of the data obtained through a measurement run with a respective non-destructive measuring method, influenced by subjective factors.

Finally, the common, superimposed occurrence of several types of defects or deficiencies such as corrosion and cracks, especially in more complex geometries such as weld seams, is particularly problematic. Against the background of ever-increasing demands regarding the safety of pipelines, for example, the combined occurrence of defects involves high safety discounts with respect to burst pressures. In this case, a pipeline is usually operated well below the maximum permissible pressure.

In addition, approaches are known from scientific, i.e. theoretical, consideration in which the most accurate possible simulation of the measured signals is to be achieved using forward models via successive variation and iterative methods of an assumed defect geometry. In this case, neural networks are used, for example. Theoretically, these approaches can result in solutions in the sense of a resulting defect geometry, but these solutions are not necessarily realistic. This is particularly true for complex data sets which, under certain inverse problems, lead to unexpected, exotic, and incorrect solutions. While such scientific models provide a solution to the described problem in the form of defect geometries in precisely defined and delimited test scenarios, this has not yet been successful for real measurement data that have a large number of interfering influences.

BRIEF SUMMARY OF THE INVENTION

It is therefore the object of the present invention to show a robust way of accurately reconstructing a real defect and to calculate the load limit of an object with one or more defects as precisely as possible.

According to the invention, the geometry of one or more defects is determined by means of at least two reference data sets generated on the basis of different, non-destructive measuring methods, wherein at least one, preferably a plurality of particularly competing expert routines, each with at least one separate search strategy or at least one algorithm of its own, use an identical initial defect geometry. If several are used, the expert routines are executed, particularly in parallel, on one EDP unit. If a single expert routine is used, it can access various algorithms for adjusting the defect geometry.

Such a method according to the invention for determining the geometry of one or more real, examined defects of a metallic and in particular magnetizable object, in particular a pipe or a tank, by means of at least two reference data sets of the object generated on the basis of different, non-destructive measuring methods, comprises an at least partial representation or mapping of the object on or through an at least two-dimensional, preferably three-dimensional object grid in an EDP unit, and further comprises a determination, in particular a generation, of an initial defect geometry as the initial defect geometry. The initial defect geometry can be mapped directly on the object grating or represented by it, but it can also be present in a parameter representation, for example on an at least two-dimensional defect grid.

The various measurements are linked with one another by using a single defect geometry as the calculation basis for all data sets. A defect can preferably be described on the object grid by assigning the properties/"material" and "no material" or "material with defect" to the cells of the object grid. In addition, such a cell can be assigned a classifier with respect to the type of defect (corrosion, crack, or lamination defect) that may be present.

Furthermore according to the invention, a determination, in particular a generation, of respective prediction data sets, that is to say data sets matching the non-destructive measuring method, is carried out to obtain initial prediction data sets on the basis of the common initial defect geometry. This is done by simulating or assigning a measurement that matches the respective reference data set.

Then an iterative adjustment of the initial defect geometry to the geometry of the real defect or defects takes place by means of the EDP unit, this adjustment preferably being carried out by means of the at least one, preferably by means of the several expert routines that are in competition with one another and in particular that run parallel to one another, whereby in the or respective expert routines by means of at least one own algorithm or own search strategy and on the basis of the initial defect geometry a respective expert defect geometry is generated.

The expert routine has its own algorithm if at least one of the algorithms available to the expert routine for adjusting the defect geometry differs at least partially from the algorithms of another expert routine. Preferably, stochastic processes can be used to differentiate the algorithms of different expert routines. Each expert routine has at least one algorithm for adjusting the defect geometry; preferably, several algorithms are available to at least one expert routine. An algorithm based on stochastic processes can also be selected or specified within an expert routine.

According to the invention, a respective expert prediction data set is determined on the basis of the respective expert defect geometry, in particular by simulation or assignment of a measurement that matches the respective reference data set, wherein the expert defect geometry on which the respective expert prediction data set is based is made available to at least one, preferably several and in particular all of the expert routines as a new initial defect geometry for further adjustment to the geometry of the real defect or the real defects, if the respective expert prediction data set is more similar to the respective reference data set than the corresponding initial prediction data set and/or at least one fitness function that takes into account two sets of expert prediction data is improved. Subsequently, i.e. for the next comparisons of the respective expert defect geometries with the new initial defect geometry in the iteration, the expert prediction data sets belonging to the new initial defect geometry are used as new initial prediction data sets.

A measure of the similarity can also be formed via the fitness function, such that in one embodiment variant, for example, a new initial defect geometry is provided by an expert routine for the further iteration steps if there is an approximation of only one of the simulated or assigned expert prediction data sets to the respective reference data set.

A simple comparison of the expert prediction data sets with the reference data sets based on the expert defect geometry results, for example, as follows:

$$E = \sum_i |Y_{cal}^i(x_1 \ldots x_n) - Y_m^i|,$$

wherein $Y_m^i$—is the (geometrically usually two-dimensional measurement data i signal) of the i-th measuring method and $Y_{cal}^i$—is the simulated signal of the associated measuring method. Furthermore, the defect geometries varied via one or more expert routines are referred to as $x_1 \ldots x_n$. The smaller E, the better the calculated defect geometries match those actually present.

The iterative adjustment by means of the expert routines takes place until a stop criterion is met. According to the invention, (assigned or in particular simulated) expert prediction data sets generated based on the same initial defect geometry are compared to the respective reference data sets in a measuring method-specific manner, thus avoiding the disadvantages of the separate evaluation known from the prior art. In the measuring method-specific comparison, for example, a simulated EMAT scan is compared to the EMAT reference data set obtained on the basis of the real measurement, a simulated MFL scan is compared to the MFL reference data set obtained on the basis of the real measurement, etc.

By accessing the same defect geometry and the automated and combined analysis of the various measuring methods, the burst pressure of the examined object can be calculated at least 10%-20% more accurately and, for example, a pipeline can be operated with higher pressures. In addition, the examined object has to be inspected less often, e.g. by excavation, due to the automated, combined consideration of the reference data sets of different measuring methods and the resulting improved description of the defect or defect geometries. In addition, the combined evaluation of data obtained on the basis of different measuring methods minimizes the problem of singular, local solutions, i.e. the determination of the defect geometry is more robust.

Different non-destructive measuring methods are the aforementioned MFL, EMAT, UT, and EC measuring methods. The method according to the invention is particularly characterized in that a data set based on an MFL, eddy current, EMAT or ultrasonic measuring method is used as the first reference data set and a data set generated on the basis of another measuring method from this group of measuring methods is used as the further reference data set. If a measuring method such as an EMAT method generates a data set with several sub-data sets, for example sensors recording several signals, then preferably all sub-data sets are used in the method.

Reference data sets from the following measuring methods are preferably used for the joint consideration of corrosion and cracks in particular:

a) a first reference data set based on an MFL measurement and another reference data set based on an EMAT measurement, or b) a first reference data set based on an MFL measurement and another reference data set based on an UT measurement, or c) a first reference data set based on an MFL measurement, as a first other reference data set one based on an EMAT measurement, and as a second, other reference data set one based on an EC measurement.

The reference data sets generated on the basis of MFL measurements can preferably also be differentiated with respect to the direction of magnetization, i.e. the variants a), b) or c) can either be a reference data set based on an MFL measurement with magnetization in the axial direction (MFL-A measuring method) or on the basis of a measurement with magnetization in the circumferential direction (MFL-C measuring method). Reference data sets obtained "on the basis" of a specific measuring method come from respective measuring runs ("scans") and are possibly prepared for automated processing in the method according to the invention, e.g. their values can be normalized, Fourier transformed, and/or interpolated for the purpose of adjusting to specific grid geometries. In particular, they are available as two-dimensional data sets with respective length or width or circumference information and measured values assigned to them. In the case of reference data obtained using EMAT methods, the reference data sets are preferably amplitudes ("counts") integrated over time at the respective wall positions or measurement positions, the so-called A-scans.

The expert prediction data set can be determined within the workflow of the expert routine and/or via a program module controlled separately by a monitoring routine.

Advantageously, different and defect-specific variations for generating the respective expert defect geometry are carried out in the expert routines, which are particularly in competition with one another, wherein a first expert routine is provided for varying cracks, another for varying corrosion, and/or another for varying laminating defects. Laminating defects, which have a disruptive effect in the form of non-interconnected layers of an (object) wall, e.g. in EC measurements and particularly are discovered by special modes of EMAT measurement, can thus be taken into account separately and particularly are not taken into account for the consideration of the remaining service life, e.g. of a pipeline.

The determination of the expert prediction data set on the basis of the respective expert defect geometry is also particularly carried out if there are no sufficiently large databases available with calculated or measured data on the respective defect geometries, by simulating a measurement that matches the respective measuring method, which is described below for further developments of the invention.

Alternatively, the expert defect geometry can also be assigned an actually measured data set from a sufficiently extensive database if a corresponding geometry with a measurement that also fits the material boundary conditions is present in this database. A combined approach is also possible in which a database is first searched for measurement data that are already available and a simulation is only carried out if the search was negative. Overall, this can lead to a quick determination of the respective expert prediction data set.

The method according to the invention is carried out completely and particularly in an automated manner on an EDP unit, which can optionally consist of multiple computers. The associated computer program can be a single program or it can be a program package comprising a plurality of program modules which, for example, run on different EDP systems or subunits depending on resources and can be stored there on respective EDP media. In particular, a computer has the typical means of a data processing unit such as one or more processors, at least temporary memories (RAM), data communication means, display and/or input units. While the selection of the reference data set can preferably take place in a user-controlled manner, the defect geometry is determined automatically during the iterations. Before the actual iteration, program parameters for selecting the algorithms available to the expert routines, for determining an initial defect geometry, for determining the first prediction data set and/or an expert prediction data set that show the respective simulated measurement data can preferably be defined. For example, it can be determined in this way whether the determination of the initial prediction data sets is to be created via a simulation of a respective non-destructive measurement on the basis of a grid representing the object with the defect or whether it is to be loaded from a database, for example via a regression. For example, in the case of the simulation of an MFL field, the parameters required for comparison to the reference data set can be defined, such as direction of magnetization, strength of magnetization, distance of the sensor from the object surface and/or speed of the measuring device.

According to a further development according to the invention, the expert routines competing with one another for resources of the EDP unit, which each use their own search strategies to find their own solutions for determining the geometry of the real defect, particularly avoid the problem encountered with the theoretical approaches from the prior art that isolated solutions are found. Compared to the separate, manual evaluation of the data sets, the solution found is not only significantly better, but also easier to understand and document. Singular solutions, in which an algorithm of whatever type does not get any further and the defect geometry is still not reproduced realistically, are avoided in this way.

The method according to the invention is preferably further characterized in that simulation parameters and/or material-specific parameters of the object obtained from a calibration run of the inspection device belonging to the measuring method are used for the measuring method-specific generation of the initial and/or expert prediction data sets. These include, for example, the distances and angular position of a respective sensor in relation to an object wall and/or magnetic field curves.

A representation of the object on or through a three-dimensional grid is usually necessary for a simulation of the leakage flux, EMAT, UT, and/or EC data associated with a geometry. In this grid, the representation is performed at least partially, in the sense that at least the part of the object with the defect or defects and preferably adjacent areas are represented by or on the object grid, for example by assigning a property "material" or "no material" to the cells of the grid. As an alternative, the simulation of the non-destructive measurement can also be derived from a parameter representation of the defect geometry. Finally, the leakage flux data can also be determined via a database query, for example by means of a regression function. This also applies to the simulation or assignment of the EMAT, EC, and UT measurement data belonging to a geometry.

In the expert routines, a parameter representation of a respective defect, derived from or assigned to the initial defect geometry, is preferably varied to generate the expert defect geometry. The variation of a parameter representation of a defect, preferably with subsequent transfer of the parametric representation of the defect geometry to a particularly three-dimensional grid that can be used for the simulation of the expert prediction data set, enables a quick variation of the defect geometry as a direct change of the defect on the grid, since clearly fewer calculations need to be performed.

Inner or outer cracks or cracks in a metal wall are preferably described in a parameter representation by a connecting line between two grid nodes located on the inside or outside, wherein each crack is assigned a depth that can be specified for the line as a whole or sections thereof.

Furthermore, a laminating defect is preferably described by means of a particularly two-dimensional grid along the inner surface of the examined object. This laminating defect grid can be arranged with its nodes on the inside node points of the object grid, but it can be provided with a fixed grid node spacing for simplified viewing. In particular, a value is assumed at each node point of the laminating defect grid with the distance between the laminating defect and the inner surface, wherein a value of "0" indicating the absence of the laminating defect.

Corrosion-related defects are preferably parameterized using a two-dimensional grid with a fixed grid size, for example 3.5*3.5 mm cells. The grid can be placed on the inner or outer surface, depending on the location of the corrosion, and the depth of the corrosion is assumed at its node points.

Although the method according to the invention can be carried out for determining one or more defects within a reference data set, reference is mostly only made to one defect below for the sake of simplicity.

In particular, the defect geometries which are the basis for determining the associated expert prediction data sets are defined on the grid nodes of a two-dimensional defect grid. Due to the two-dimensional representation of the defects, the expert routines can work significantly faster than if the adjustment of the defect geometry is carried out on a three-dimensional grid.

For the simulation of the respective non-destructive measurement of a new defect geometry, the two-dimensional defect grid or the corresponding parameter representation is preferably transferred to the object grid, e.g. interpolated, wherein with the surface of the object to be displayed is adjusted to the defect depths of the defect geometry. The simulation is then calculated on the particularly three-dimensional object grid. Alternatively, the simulation can also be carried out on a two-dimensional grid or by means of a regression model which is based on a database with respective real or already simulated measurement data sets. For the (forward) simulation of the respective measuring method on the assumed expert defect geometry, finite element methods, finite difference methods, and/or boundary element methods are used in particular.

An initial defect geometry, which is alternatively obtained or specified, for example, via a look-up table, a database comparison, or particularly a one-time execution of an expert routine, can particularly be determined by a machine learning algorithm, particularly in the form of a neural network. According to the invention, an initial defect geometry, particularly on the object grid or an at least two-dimensional defect grid, is generated according to such a further development by inversion of at least parts of the reference data sets by means of a neural network trained for these tasks. The initial defect geometry can be mapped directly on the object grid or represented thereby, but it can also be present in a parameter representation, for example on an at least two-dimensional defect grid. It is also possible for the neural network to output a result vector, the vector elements of which contain information about the geometry of the defects. The defects are then mapped onto the object grid via an assignment of the vector elements. These defects are described, for example, by the fact that the cells of the object grid are assigned the property or "no material" or "material with defect." A defect is where this property is present. The initial defect geometry is determined via a direct inversion in such a way that a possible geometry is deduced by means of the neural network on the basis of the reference data sets determined by means of the respective various non-destructive measuring methods, which results in the respective measurement results in the various non-destructive measuring methods used.

A simulation routine preferably generates training data using different training geometries, with which data a neural network is trained for inversion of the measurement data. Training data include a number of training geometries that have the actual object (e.g. a pipe or pipeline wall) as well as defects in the object, weld seams, or other elements of the object relevant for non-destructive measurement processes, for example, as well as simulations of the respective measurement processes carried out on these training geometries. Furthermore, the simulation routine can use the training geometries to determine training data with different operating conditions of the non-destructive measuring method. For example, different training data for different measurement runs of the non-destructive measuring method can be simulated for a training geometry, for example with different distances between the sensor and the object. Training data can also be generated on different object geometries for a specific shape of the defect, for example in the case of an arrangement in a weld seam.

The neural network is preferably trained on the basis of data from a database containing simulated measurements. The use of already simulated measurements reduces the effort required for training the neural network, since it then only includes the actual adjustment of the neural network and not the simulation of training data as well. In addition, such a database may contain a large number of different training geometries. Data about pipe geometries and/or types of defects that occur particularly frequently are preferably contained in a respective database. By using data from such a database, the neural network is trained particularly well in detecting frequently occurring defect geometries.

Training data obtained from the simulation of different training geometries are preferably entered into such a database. This reduces the computing effort for future training runs of neural networks.

The neural network preferably converts input data with a two-dimensional spatial resolution into an initial defect geometry having a three-dimensional spatial resolution. A neural network with one or more convolutional layers and/or one or more transposed convolutional layers is preferably used for this purpose. An input layer of the neural network has a two-dimensional spatial resolution, wherein a vector with a plurality of entries can be assigned to an input point of the input layer. The neural network uses this input data to generate a three-dimensional initial defect geometry. The three-dimensional initial defect geometry can be used particularly easily for the calculation of a prediction data set by the simulation routine. A neural network can have a respective input layer for each reference data set.

Defects are preferably classified. The identified defects are assigned specific information about the defect to this end. Defects can be differentiated, for example, into surface defects such as corrosion and defects in the volume such as cracks, inclusions or delaminations/laminating defects. This makes it possible to describe the different types of defects, if necessary, in a subsequent iterative adjustment of the initial defect geometry using different defect models. As a result of the additional information, the adjustment of the initial defect geometry in the subsequent iterative method can be more robust, simplified, and/or accelerated.

According to a further development of the method according to the invention, the object grid is also generated automatically from the reference data sets. To determine the object grid, anomaly-free areas and anomaly-afflicted areas of the object are first classified on the basis of at least parts of the reference data sets, wherein an initial object grid is created particularly on the basis of previously known information about the object, using the initial object grid to calculate prediction data sets for the respective non-destructive measuring methods, a comparison of at least parts of the prediction data sets with respective parts of the reference data sets is carried out, excluding the anomaly-afflicted areas, and depending on at least one degree of accuracy, the initial object grid is used as the object grid describing the geometry of the object, or an iterative adjustment of the initial object grid to the geometry of the object is carried out by means of the EDP unit in the anomaly-free areas.

Anomaly-afflicted areas of the reference data sets are spatial areas to which measurement data that differ significantly from neighboring areas are assigned. It is believed that these anomalies are due to defects. Anomaly-free areas are preferably contiguous areas in which the measured values measured by the non-destructive measuring method do not change or only change within a specific tolerance range in which the gradient of the change remains below specific limit values, the deviation of individual measured values from a mean value is less than a specific threshold value and/or the deviation of a mean value in a local area from the mean values of adjacent local areas is below a threshold value.

According to the further development according to the invention, an initial object grid can be created for determining the object grid, using previously known information about the object, in the case of pipelines, for example, the pipeline diameter and the wall thickness. Measurements that match the respective reference data set are simulated on the basis of the initial object grid. Subsequently, at least parts of the prediction data sets are compared to at least respective parts of the reference data sets, wherein the anomaly-afflicted areas of the reference data sets or of the object are excluded from the comparison. If the compared data coincides with sufficient accuracy, the initial object grid is viewed as a sufficiently accurate representation of the actual shape of the defect-free object and can furthermore be used as a basis for determining the defects. Otherwise, an iterative adjustment of the initial object grid to the geometry of the object in the anomaly-free areas takes place in the EDP unit.

A new initial object grid is preferably created for this iteration and new prediction data sets are in turn calculated for this. A renewed comparison of at least parts of the new prediction data sets with at least respective parts of the reference data sets, excluding the anomalous areas, takes place until an object stop criterion for the iterative adjustment, for example in the form of a measure of accuracy, is reached or fulfilled. The initial object grid then present is then used as the object grid describing the geometry of the object.

To obtain an initial object grid that represents the defect-free examined object in the evaluated section or in its entirety, information from the reference data sets and/or the object grid is preferably interpolated or extrapolated from the anomaly-free areas into the anomaly-afflicted areas. For example, after the classification of the reference data sets into anomaly-afflicted and anomaly-free areas, the information from the anomaly-free areas can be interpolated and/or extrapolated into the anomaly-afflicted areas and an auxiliary reference data set obtained in this way can be used for determining the object grid. It is also conceivable to initially create an object grid only for the areas classified as anomaly-free. This object grid has gaps in the anomaly-afflicted areas, which gaps can then be closed by means of interpolation or extrapolation from the anomaly-free areas. In this way, an object grid representing the geometry of the object is obtained, which can then be used for further analyses of defects or defect geometries in the anomaly-afflicted areas.

In the classification of anomaly-free areas of the reference data sets, an anomaly-free area is preferably assigned to at least one predefined local element of the object. This is used when creating the initial object grid or inserted into the initial object grid. This step simplifies the process of creating an initial grid. As described above, the object examined by means of the non-destructive measuring method can contain weld seams, installations and/or attachments, or have a locally modified geometry that is otherwise previously known. The creation of the object grid can be facilitated if this previously known information is used. For this purpose, respective elements, such as weld seams, attachments such as support elements, brackets, reinforcing elements or, for example, sacrificial anodes of a cathodic rust protection, as well as sleeves attached for repair purposes, are predefined in their shape and/or extension. The measurement results of the non-destructive measuring methods naturally look different in these areas than in areas of an unchanged wall of the object, for example the pipeline wall in the case of pipelines. However, these changes are uniform and large in area compared to most defects. Furthermore, they can be expected because the position of the elements causing the change is known.

An identification can be carried out in the classification by specifying the local elements, as to whether these are, for example, a weld seam or a support structure. The element identified in this way can then be used with its known general shape or general dimensions when creating the initial object grid, or it can subsequently be inserted at the appropriate points in the initial object grid to adjust it to the actual shape of the examined object.

The respective local element, particularly in the form of a weld seam, is particularly preferably described by means of a parametric geometry model. This can significantly reduce the effort involved in creating the object grid. The previously known information about the local element is used for this purpose. A weld seam can be known, for example, as extending in the circumferential direction around the object and can be described with sufficient accuracy by a weld seam width and an elevation. A predefined parametric geometry model of a local element can thus be adjusted to the actual local shape of the object by varying just a few parameters. The process for creating an object grid is thereby significantly accelerated. Particularly in the case of an iterative adjustment of the initial object grid, only one or more parameters of the parametric geometry model can be changed. The variation of individual parameters can also be limited by specific limit values within which these can be modified. Such a limitation can minimize the risk of obtaining physically nonsensical results. The reliability of the method is increased.

When performing the method according to the invention, the measurement data prediction data sets corresponding to the reference data sets are determined as initial prediction data sets, particularly by simulating a respective measurement, for the assumed initial defect geometry. The simulation of the individual non-destructive measurements is carried out, for example, using a finite element model as a forward calculation. In the simulation of a leakage flux measurement, for example, the parameters required are specified in accordance with the real measurement. This applies particularly to the direction of magnetization, the magnetic field strength and/or the distance between the sensors above the surface of the object. For a simulation of an EMAT measurement, among other things, magnetic field strengths, directions of magnetization and sensor positions are specified as well. A respective initial prediction data set then results as a simulated leakage flux measurement on the basis of the initial defect geometry. This data set could already be compared to the reference data set of the object, which, however, often does not lead to meaningful solutions at the beginning or before the iteration, since the initially assumed defect geometry is not yet precise enough.

The initial defect geometry is included as the initial defect geometry in the iterative approximation process of the competing expert routines. The expert routines themselves are, for example, independent of one another as separate program modules without direct interaction with one another and can be equipped with resources, particularly with computing time, depending on a monitoring routine or a main module.

Based on the expert defect geometry developed in a respective expert module, expert prediction data sets are in turn determined for each of these geometries in particular. Thus, for each expert defect geometry, which is available particularly as a 2D data set of depth values of the defect and/or as a parameter representation, the respective expert prediction data set is assigned or generated as simulated measurements. The simulation of the respective measurements based on the respective expert defect geometries takes place in accordance with the above-described calculation of the initial prediction data sets. Particularly, the calculations are carried out in parallel based on the respective expert defect geometries. This can go hand in hand with the construction of a database in which the simulation data belonging to the respective defects is stored with the aim of being able to save computing time later and for other similar data.

Before generating the expert prediction data sets, it can be advantageous to adjust, particularly to partially refine, the underlying grid, particularly the defect grid, and possibly also the object grid, for the calculation of the expert defect geometry. Particularly, mesh morphing techniques are used in which the object or defect grid is refined by grid point shift and/or grid point division, particularly in areas of strong gradients, to enable a more accurate determination of the geometry or a more accurate simulation below. In other areas with weaker gradients, the grid can be made coarser to save computing time. The grid used is automatically adjusted for optimal evaluation of the defect geometry. At the same time, a significant reduction in the number of unknowns is achieved, such that computing time is saved again.

Furthermore, according to a further development according to the invention, the parameter representation of one or more defect geometries can be transferred to the object grid in advance, such that, on the one hand, a numerically comparatively less complex adjustment of the defect geometry can be carried out in the expert routines, while the geometry of the object can be calculated as exactly as possible in the forward simulation for the respective measuring method.

If the comparison between the reference data sets and the respective expert prediction data sets of an expert routine shows that these, possibly as described above, are closer to the reference data sets than the previous initial prediction data sets, depending on a fitness function, then the associated expert defect geometry is used as the initial defect geometry for the others as well as for the respective expert routine. Based on this solution, this geometry is started in a next iteration step, unless another expert routine has, for example, found another, once again better solution while its own defect geometry determination is still in progress, which is then made available to other or all expert routines.

In the case of the expert routines that are particularly competing with one another, preference is given to those with respect to the resources available to the EDP unit which, as described below, are more successful in approximating the real measurement data than other competing expert routines. Resources of the EDP unit are particularly the CPU or GPU time and/or a prioritization in memory allocation.

The expert routines (on the EDP unit) advantageously run in competition with one another in such a way that the distribution of the resources of the EDP unit, particularly in the form of computing time, to a respective expert routine as a function of a success rate, particularly the number of the initial defect geometries calculated by the expert routine and made available to one or more other expert routines is taken into account, and/or takes place as a function of a reduction in a fitness function in which particularly the number of expert prediction data sets generated for the reduction is taken into account. The competition between the expert routines results particularly from the fact that the program part designed as a monitoring routine then increasingly allocates resources to the respective expert routines, particularly in the form of computing time, preferably CPU or GPU time, if these are more successful than other expert routines. An expert routine is successful when it has found a defect geometry provided, for example, with a simulated EMAT measurement that is more suitable to the reference data set and is made available to the other expert routines.

From this it can emerge, for example, that individual, particularly successful expert routines receive more than 50% of the total available computing time, which significantly reduces the overall duration of the method according to the invention. At the same time, the program can specify that none or some of the expert routines do not reach a specific percentage of computing time to avoid the problem of singular and exotic defect geometries or results from the individual routines. In the event that a previously successful expert routine only finds a local and not a global solution, a way can be found out of the blocking situation that otherwise occurs in the prior art.

The adjustment by means of the expert routines takes place until a stop criterion is met. This criterion is, for example, a residual difference with respect to the measured and simulated measurement data. It can also be an external stop criterion, for example based on the available computing time or a particular predeterminable number of iterations or a particular predeterminable or predefined computing time or a computing time determined from the available computing time. The stop criterion can also be a combination of these criteria.

It has been found that the accuracy of the defect determination is qualitatively improved by the method according to the invention. A calculation of the maximum load capacity resulting from this shows that pipelines, for example, can be operated much more economically, i.e. at higher pressures. The accuracy of the defect determination is significantly increased. Maximum operating pressures resulting from the simulated defect geometry according to the method described above and below can be set by at least 10%-20% and particularly by up to 50% higher, which significantly reduces the maintenance and servicing costs for the operation of the pipeline and its operator. For the first time, an adequate determination of the ASME B31G-2012 level 2 approach ("river bottom profile") for the "remaining strength algorithm" can now also be implemented for MFL data sets.

In addition, the method according to the invention makes it possible, in an improved manner, to better estimate the change, i.e. the development, of the defect. The precise spatial description of the defect geometry on a three-dimensional object grid allows a further improvement in accuracy of 10%-20%, especially with an FEM-based forward simulation. Furthermore, better differentiation between cracks and corrosion-related defects prevents a corrosion-related defect incorrectly identified as a crack from having to be examined on site, for example by excavation.

The resources of the EDP unit are preferably distributed, particularly in the form of CPU time, to a respective expert routine as a function of the number of initial defect geometries made available by this expert routine to all expert routines. This can be, for example, a number of slots for calculating the expert prediction data sets in the form of simulated measurement data sets, the number of processor cores processing the computing task in parallel, or the like. Furthermore, within the framework of the computer program product implementing the method according to the invention, the program adjusts to the resources available in the EDP units in the form of processor cores, memory space, memory architecture, graphics cards, etc. Detection of the real defect geometry is significantly faster by prioritizing particularly preferred expert routines and their algorithms.

To minimize the problem of singular, local solutions even further, another reference data set which is independent of the first MFL reference data set is created in addition to a first reference data set based on an MFL measuring method and another reference data set based on another measuring method to determine the geometry of the defect or defects based on MFL. The MFL data sets are linearly independent if they were generated by MFL measurements with magnetizations of the object at an angle to one another. The magnetizations are angled to one another if the respective mean induced magnetic field strengths in the examined area are not parallel or congruent. Particularly, the angle is between 400 and 140°, preferably between 80° and 100° and particularly preferably 90°. Based on the initial defect geometry, three initial prediction data sets are determined, particularly by means of another MFL simulation that takes into account the linear independence, i.e. particularly the different magnetizations, and an expert defect geometry is only used as the initial defect geometry if the associated expert prediction data sets determined for both independent magnetizations and the expert prediction data set for the other measuring method are more similar to the respective reference data sets than the initial prediction data sets determined for the two magnetizations and/or a fitness function taking into account the expert prediction data sets is improved. The risk of singularities is further reduced due to the parallel or associated processing of the two linearly independent MFL data sets and the reference data set of another measuring method, preferably designed as an EMAT method, and the use of an identical initial defect geometry, the simulated measurement data of which must be better overall with respect to a similarity or a fitness function. At the same time, the quality of the initial prediction data sets available to all expert routines improves. The number of iterations can thus be further reduced.

Particularly, the first MFL reference data set is generated via an MFL measurement with axial magnetization and the second MFL reference data set is generated via an MFL measurement with magnetizations in the circumferential direction of the pipe. The magnetizations of the pipe or of an object are at right angles to each other, such that maximum information content can be obtained from the magnetic leakage flux measurements, which content is fully available through the simultaneous consideration of the respective reference data sets and the simulated expert prediction data sets during the calculation. The method steps described below run analogously, taking into account the above, when using multiple reference data sets that have arisen on the basis of linearly independent magnetizations and other measuring methods.

The measurement simulations are carried out quickly through the use of initial and/or expert prediction data sets based on a forward model to simulate the respective measuring method, particularly by means of a finite element model. The simulation, for example, of the leakage flux measurements based on the expert defect geometries can be implemented using a separate program module which, in particular, is controlled and/or monitored by a monitoring routine and called up separately by the individual expert routines. There can also be several modules that are distributed over individual computer units and made available to a respective expert routine.

Advantageously, after an adjustment of the defect geometry, a refinement of the object and/or the defect grid can take place in the areas in which the depth of the assumed defect or defects exceeds a threshold value, wherein this threshold value is specifiable such that only gradients above a specific size lead to a change in the grid. With such a refinement, particularly the total number of gradients of a new expert defect geometry can be taken into account to achieve a balance between the adjustment of the respective grid, particularly the object grid, and the subsequent computing operations.

The refinement of the grid with the aim of reducing computation time can take place both on the basis of an initial reference data set and before the expert prediction data set is calculated. A separate program module or individual sub-modules of the respective expert routines can be provided for this as well.

Particularly, the refinement of the object and/or defect grid particularly advantageously reduces the required CPU time by shifting and/or dividing grid points by significantly reducing the number of independent variables that have to be used in the forward algorithm to simulate the non-destructive measurement. A grid point shift can also be used to adjust object or defect grids.

A fitness function is preferably used as a measure for the similarity of the expert prediction and reference data sets to effect a comparison of the simulated and measured data sets based on standard routines and respectively quickly, i.e. while saving computing time.

Particularly, the initial defect geometry or a pointer referring thereto is stored in a memory area of the EDP unit that is accessible to all expert routines. This memory area is in turn under the control of a monitoring routine, such that individual expert routines can also be prioritized in this respect.

Instead of using the initial defect geometry every time at the beginning of a new iteration, which is stored, for example, in a central memory area accessible to all expert routines, at least one expert routine can adjust its own expert defect geometry while refraining from adopting the initial defect geometry at the beginning of a new iteration in a further development of the method according to the invention. For this purpose, an expert routine can have a functional rule in which, for example, an opposing strategy is specifically selected depending on search strategies used in other expert routines. In such an event, the expert routines can influence each other indirectly. Such a procedure can be particularly advantageous if it is found that a routine that has always been successful up to now favors an unrealistic solution. This can be detected, for example, on the basis of impermissible values relating to the depth of a defect. If an expert routine which does not adopt the initial defect geometry does not deliver any improved solutions, it is automatically down-prioritized such that less and less computing time is made available to it.

A change in the initial defect geometry or, more generally, in the geometry of the defect and/or object grid, which does not occur after a plurality of iterations and is to be designated as substantial, can preferably be assumed as a stop criterion or as a convergence criterion. The solution found up to that point then is the best. The stop criterion is preferably chosen such that the observed variations in the simulation of the measurement results that lead to the refinement of the object or defect grid are substantially below the variations that result from the individual measurement spread, for example by a factor of 2, and which, for example, are individually specified on the basis of so-called "essential variables" of the API 1163 standard This ensures that the accuracy of the final model is in the range of the accuracy specified by the measurement itself. Accordingly, a comparison of the variation of the expert prediction data set with the measurement spread of the real data set is preferably used as the stop criterion. The stop criterion causing a program stop and particularly an output or storage of the initial defect geometry calculated up to that point can preferably be specified by program parameters which can be set in advance.

Particularly, multiple algorithms for adjusting the expert defect geometry are available to an expert routine. This can involve approaches from the field of machine learning, stochastic optimization, empirical and/or numerical model functions. Particularly, empirical values from evaluators can also be used in the expert routines. Defect-specific variations as described above preferably take place in one or more expert routines, i.e. individual algorithms are designed for the variation of corrosion, cracks, and laminating defects. This creates a sufficiently diverse approach with which all solutions can be taken into account in a targeted manner and under competitive conditions.

The object set at the beginning is also achieved by a method for determining a load limit of an object that is at least under pressure during operation and particularly designed as an oil, gas, or water pipeline, wherein the method uses a data set describing one or more defects as an input data set is used in a calculation particularly designed as a forward modeling of the load limit, wherein the input data set is initially generated according to the method described above or below for determining the geometry of a defect. The advantageous representation of the defect geometry, particularly as a non-parameterized real three-dimensional geometry or as a two-dimensional surface with respective depth values, makes simplifications previously assumed to be necessary in the industry superfluous, such that for this reason, too, an increase in the accuracy of the defect determination as a whole has not been ensured in an attainable manner.

If accuracy was previously limited to the specification of the point of the maximum depth of the defect, the entire profile is now determined with high accuracy. Typically, the accuracy of the maximum depth is reduced to the level that can be achieved depending on the measurement accuracy, i.e. approximately ±5% of the wall thickness compared to previously approximately ±10% of the wall thickness in the case of sizing according to the prior art described above. However, the prediction of the load limit, depending on the geometry of the defect, achieves increases in accuracy from, for example, previously ±50% to now ±5%, particularly for critical cases. The advantage according to the invention thus lies particularly in an adequate representation of the defect geometry, which is achieved for the first time and which precisely enables this increase in the first place.

BRIEF DESCRIPTION OF THE DRAWINGS

Reference is now made more particularly to the drawings, which illustrate the best presently known mode of carrying out the invention and wherein similar reference characters indicate the same parts throughout the views.

DETAILED DESCRIPTION OF THE DRAWINGS

Individual features of the exemplary embodiments described below can, in combination with the features of the independent claims, also lead to further developments according to the invention.

Figure 1:
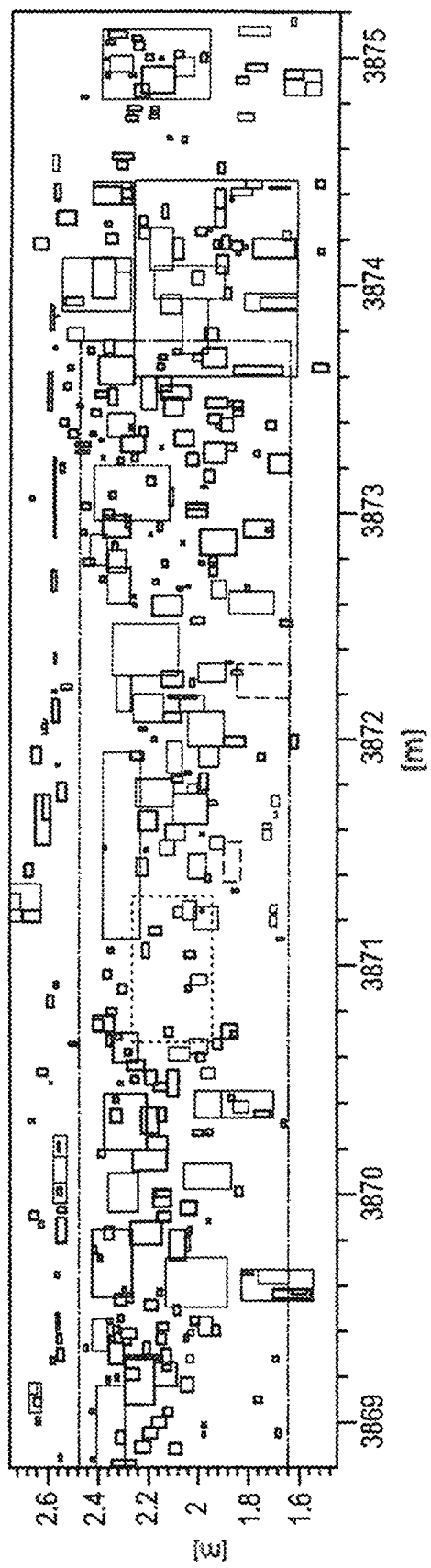
FIG. 1 shows a schematic view of a defect determination according to the prior art.

In the prior art, the evaluation of, for example, MFL data of a pipe according to FIG. 1 is carried out by means of the particularly experience-based definition of boxes. The boxes shown in the figure have respective dimensions in terms of length, width and depth. The x and y axes are shown in meter units ([m]). A check of the actual defect geometry on which this evaluation is based by means of a laser scan, i.e. by means of a direct measurement, has shown that the burst pressure of 4744.69 kPa that can be determined based on the defect geometry assumed by the MFL data evaluation is only 55.2% of the burst pressure calculated on the basis of the actual geometry. Due to the prior art, the operating pressure for safe operation of the pipeline, which results from the experience-based evaluation of 3621.29 kPa, is well below a potential safe operating pressure.

Figure 5:
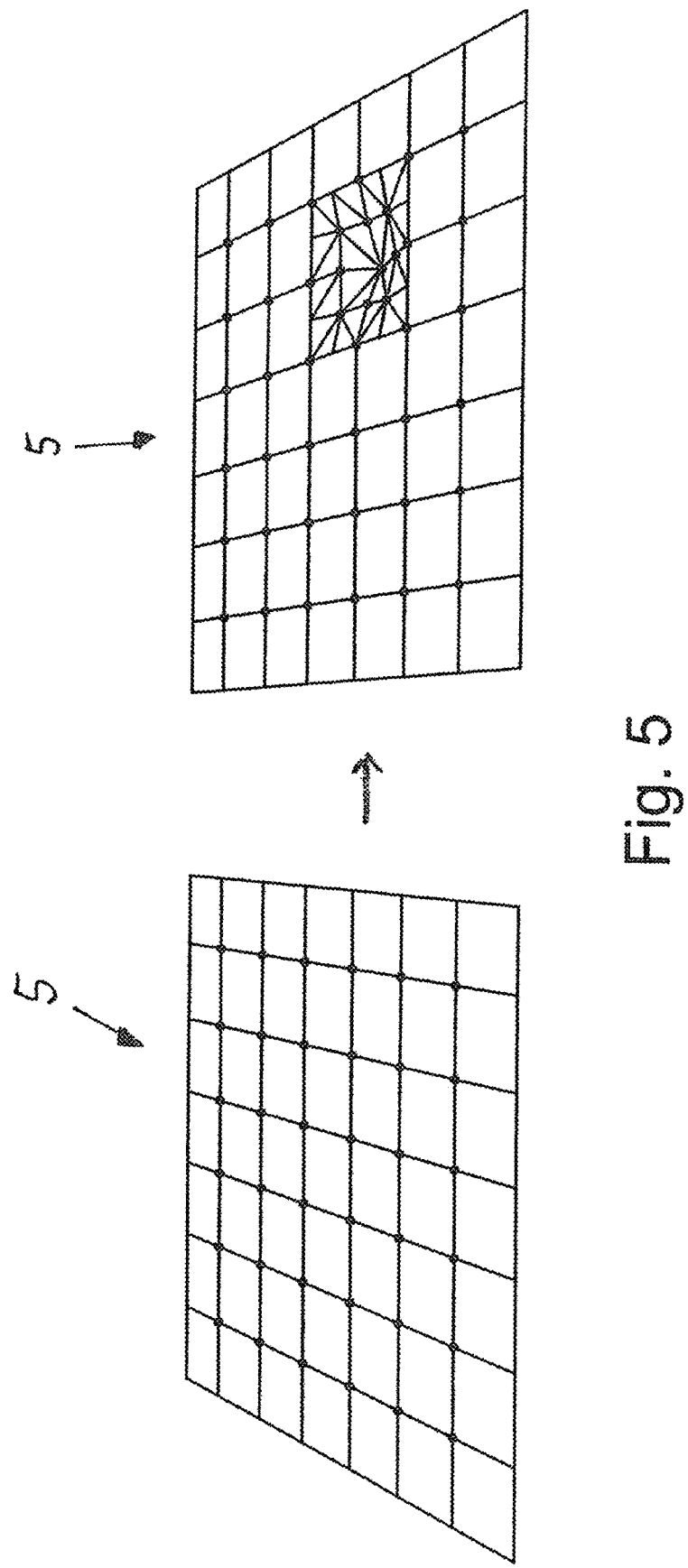
FIG. 5 shows a schematic representation of a grid refinement as part of the method according to the invention.

According to an exemplary embodiment of the method according to the invention, the surface of a pipe is represented by a 2D mesh surface. The defect geometry can be parameterized as a vector of depth values D that lie on a defect grid 5 (FIG. 5). This defect geometry is compared to the initial defect geometry based on a result for a fitness function $F(x_1 \ldots x_n)$ that takes into account measurement and simulation data belonging to the respective geometry. It is assumed here that the lower the value of a fitness function, the closer the assumed expert defect geometry is to the real geometry:

$$F(x_1 \ldots x_n) = \sum_i \|Y_{cal}^i(x_1 \ldots x_n) - Y_m^i\| + R(x_1 \ldots x_n)$$

Herein, i is the number of data sets to be treated simultaneously (real or simulated data sets), $Y_{cal}^i$ is the result of a simulation of the corresponding i-th measurement, $Y_m^i$ is the measured data of the respective reference data sets, and $R(x_1 \ldots x_n)$ is a regularization term, which can be used in the case of ambiguities, e.g. due to several minima, and can be used as follows:

$$R(x_1 \ldots x_n) = \alpha \|(x_1 \ldots )x_n\|,$$

where α is a scaling term.

Figure 2:
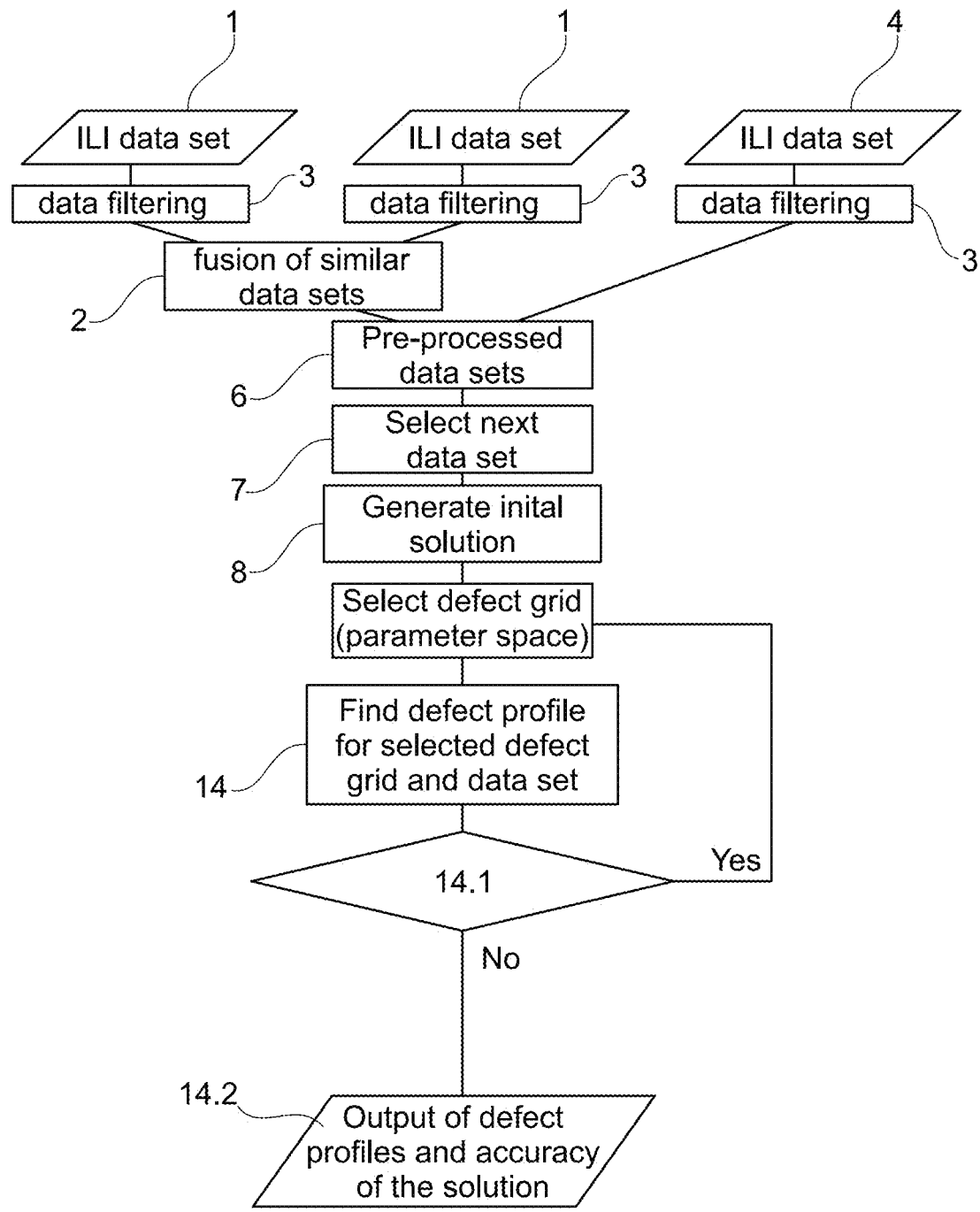
FIG. 2 shows a schematic representation of a method according to the invention.

The process sequence according to the invention is described at least in sections below according to FIG. 2, wherein a plurality of the parallel and competing expert routines 11 are described as having only one block 14.

For example, several runs of the same MFL pipeline pig can be combined as input data sets according to box 2. Both data sets 1 can be filtered beforehand for the purpose of better merging and adjusted to one another (method step 3), for example to reduce any artifacts or background noise. In addition, another data set 4 is processed based on another measuring method as an additional reference data set in the associated box 3 and filtered for the purpose of matching to identical grid structures, such that, according to method section 6, two matched reference data sets are available that were created on the basis of different non-destructive measuring methods.

Data sets that are precisely matched to one another can be treated jointly, wherein the method according to the invention implements the simultaneous treatment of the data sets by using a fitness function that takes into account the data sets to be considered together.

In step 7, the reference data sets present in step 6 are accessed, for which purpose a starting defect geometry is first determined as the initial defect geometry in step 8. As described above, this takes place based on a neural network into which the reference data sets are read as input data sets.

The solution of the neural network is then made available as one or more initial defect geometries $x_1 \ldots x_n$ to the individual expert modules. In advance, the number of parameter values that describe the defect geometries can be kept as small as possible, with the aim of reducing computing time. This is achieved, for example, by a dynamic grid adjustment. Since the number of depth values corresponds to the number of node points in the defect grid 5, the number of nodes can at the same time also be the number of defect parameters. Starting with a comparatively coarse grid, this is gradually refined in relevant areas.

The refinement shown in the relevant grid area in FIG. 5 can be achieved for an exemplary specified node point distance of 14 mm, an associated grid cell size of 14 mm×14 mm, and defect limit values of 30%, 50%, and 80% of the wall thickness, for example, wherein those cells that exceed the above depth values are successively subdivided. The grid deformation then correlates with the assumed defect geometry, i.e. in areas of large gradients there is a larger number of grid points.

After a defect grid made available centrally to all expert routines has now been selected, a new expert defect geometry is then calculated in step 14 for specific defects in the respective expert routines, and it is checked under 14.1 whether this needs to be made available to the other expert routines. This is the case if, for example, a fitness function has been improved as described above and no stop criterion has yet ended the defect finding process. In this case, the iteration continues with the defect geometry or geometries made available to all expert routines. Otherwise, the method is ended in 14.2. with the determination of the defect geometries and, in particular, the specification of the accuracy of the solution. In addition, the burst pressure can be calculated based on the defect geometries found.

Figure 3:
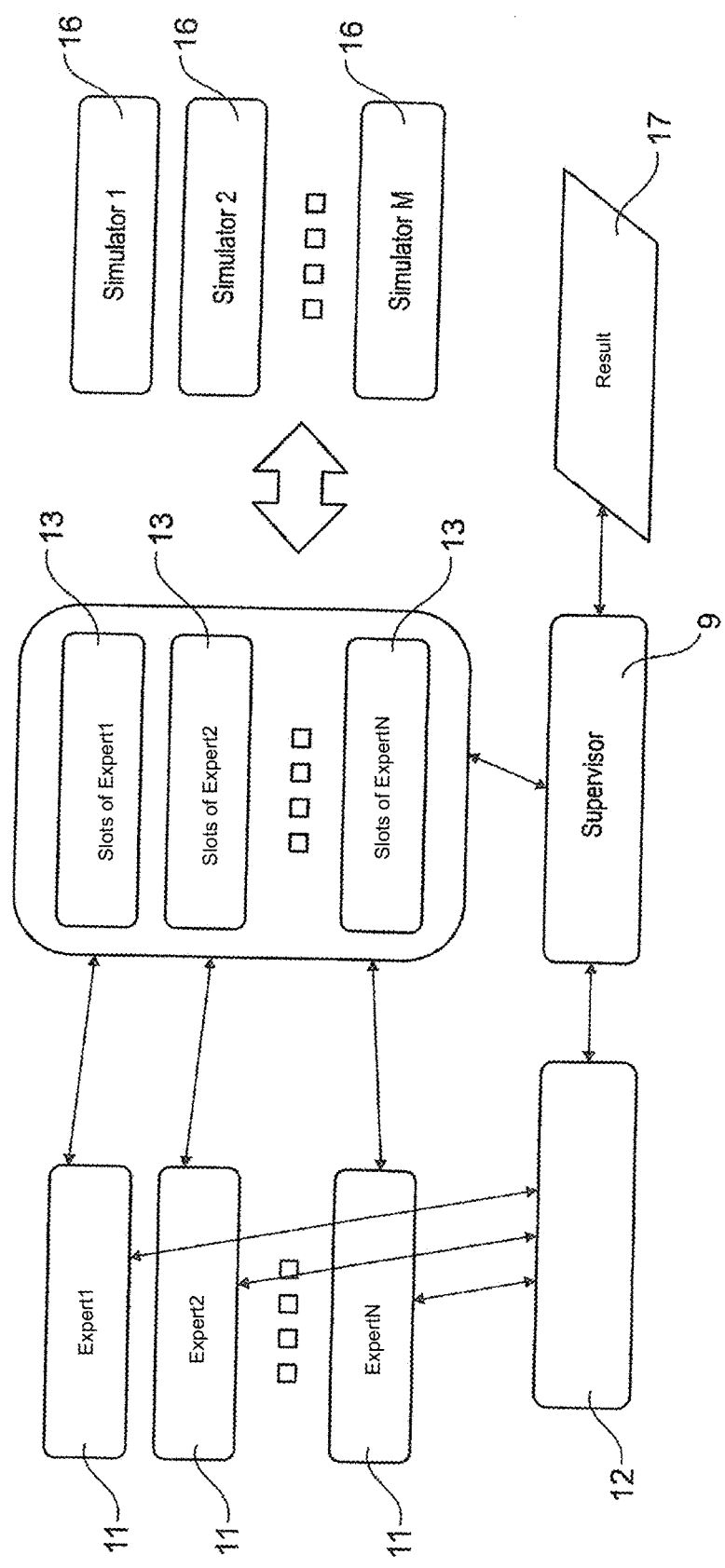
FIG. 3 shows a more detailed explanation of a portion of FIG. 2.

According to the method according to the invention, the sequence of the work flow of a group of expert routines 11 which are in competition with one another is simulated on the EDP unit. For this purpose, the program can have various modules which can set data in specific areas of the EDP unit independently of one another and particularly not synchronized with one another, so that they can be further processed there. This particularly takes place under the supervision of a monitoring routine 9 (FIG. 3). A plurality of expert routines 11 thus hold a number of computation slots 13 depending on the success defined above, i.e. for example the number of initial defect geometries written in a common memory area 12, to generate expert defect geometries and/or to be able to carry out associated MFL simulations or, in the case of an independent MFL simulation module, to have these simulations carried out. This corresponds to block 14 according to FIG. 2, wherein this block is an example of several expert routines 11 (FIG. 3). According to the present exemplary embodiment, the simulations of the measurement data that match the individual expert defect geometries are carried out based on the individual computation slots 13 in the simulation modules 16 for the purpose of creating the expert prediction data sets, also under the supervision of the monitoring routine 9. The more slots 13 are available for an expert routine, the greater the proportion of IT resources available to this expert routine. The number of program modules provided for carrying out simulations is preferably equal to the number of slots. The monitoring routine 9 monitors the number of iterations and the resulting changes in the initial defect geometry and further monitors whether an associated stop criterion has been reached. The result according to block 17, which corresponds to block 14.2 from FIG. 2, is then output.

The number of computation slots 13 available to an expert routine 11 and the simulation routines subsequently made available can vary in such a way that a first expert routine, for example, can utilize up to 50% of the total available for the computation slots and computing time available to simulation routines.

As shown, the initial defect geometries are stored in the memory area 12. This can be a memory area accessible to the expert routines 11. Log files of the expert routines 11 and monitoring routine 9 as well as instructions to the expert routines 11 can also be stored there, which are then independently implemented by them. For example, this can be an interrupt command that is set when the stop criterion is reached.

The expert routines 11 are preferably independent program modules which generate new expert defect geometries and place them in the simulation routines 16. Furthermore, the fitness function presented at the beginning can be generated in the expert routines 11 based on the expert prediction data sets and compared to the initial prediction data sets stored in the area 12. If the expert prediction data sets are overall more similar to the reference data sets than the data sets stored in area 12, these expert prediction data sets are then used as new initial prediction data sets.

For example, a new defect geometry is generated randomly in the expert routines 11. Machine learning algorithms or empirical rules can be used for this. Advantageously, however, the implementation of at least two basic expert routines working in a defect-specific manner based on the type of defect is provided to further improve the convergence of the solutions, as described below.

These search strategies, which are preferably always implemented in a method according to the invention, are based on an assumed probability distribution p(x, y) of grid points, the depth value of which results in a maximum reduction in the fitness function to determine a corrosion-based defect geometry. The probability function is used to identify N grid points $(x_n, y_n)$. Instead of grid points $x_n, y_n$, the parametric representation of the group of defects $(x_1 \ldots x_n)$ already used above can be assumed as the subject of the probability distribution, with N grid points (x, y) or $(x_n, y_n)$.

At each of the points under consideration, the depth function, which in the present case describes the depth D of the corrosion at the grid point, is changed by $\Delta D$, wherein the sign of the change is distributed randomly. The number of selected points N can also be chosen randomly:

$$D_{new}(x, y) = \begin{cases} D(x_n, y_n) \mp \Delta D, \text{ for selected points} \\ D(x, y), \text{ otherwise} \end{cases}$$

When selecting the probability function p(x, y), different expert strategies can be implemented, for example:

$$p(x, y) = \frac{D(x, y)}{\|D(x, y)\|}$$

This algorithm implements a variation of the defect depth, in which the grid points with the greatest depth are preferred. Another strategy for a corrosion-based development of the expert defect geometry may be as follows:

$$p(x, y) = \frac{H_{the\ best}(x, y) - H_m(x, y)}{\|H_{the\ best}(x, y) - H_m(x, y)\|}$$

Such an algorithm varies the defect geometry at positions at which the simulated MFL measurement signal $H_{the\ best}$ has the greatest difference to the measured signal $H_m$ for the best known solution.

On this basis, different expert routines or their algorithms can be set up by varying the number of grid points to be considered and the $\Delta D$. As an example, the following six expert routines can be used for the development of corrosion-based defects:

$$p(x, y) = \frac{D(x, y)}{\|D(x, y)\|}, N = 1 \text{ and } \Delta D = 1\% \text{ wall thickness}$$

$$p(x, y) = \frac{D(x, y)}{\|D(x, y)\|}, N = 2 \text{ and } \Delta D = 5\% \text{ wall thickness}$$

$$p(x, y) = \frac{D(x, y)}{\|D(x, y)\|}, N = 3 \text{ and } \Delta D = 5\% \text{ wall thickness}$$

$$p(x, y) = \frac{H_{the\ best}(x, y) - H_m(x, y)}{\|H_{the\ best}(x, y) - H_m(x, y)\|}, N = 1 \text{ and } \Delta D = 1\% \text{ wall thickness}$$

$$p(x, y) = \frac{H_{the\ best}(x, y) - H_m(x, y)}{\|H_{the\ best}(x, y) - H_m(x, y)\|}, N = 2 \text{ and } \Delta D = 5\% \text{ wall thickness}$$

$$p(x, y) = \frac{H_{the\ best}(x, y) - H_m(x, y)}{\|H_{the\ best}(x, y) - H_m(x, y)\|}, N = 3 \text{ and } \Delta D = 5\% \text{ wall thickness}$$

The following functional rules can be used for an expert routine that is suitable for the variation of a crack-based defect:
- the depth of the defect is randomly reduced or increased by a specific amount, preferably e.g. 1 or 2% of the wall thickness of the object,
- the position of all points of the crack is varied in a randomly selected direction, and/or
- a line describing the crack is lengthened or shortened by the position of the grid nodes on the object grid or defect grid.

An expert routine that describes a laminating defect can work according to the following functional rules:
- on the basis of the 2D parameter description of a laminating defect, the values associated with the grid nodes are varied step by step by 5% in one direction or the other with the aim of varying the position of the lamination; this can only be done for a subset of the known of the 2D description of the lamination or the laminating defect,
- randomly selected points (grid nodes) with values not equal to zero, which are in the vicinity of points with values of zero, can be set to zero (reduction of the extent of the lamination),
- randomly selected grid points with values of zero, which are located in the vicinity of grid points with values not equal to zero, can be set to the corresponding neighborhood value, whereby the lamination is increased, and/or
- all values in the grid can be moved in a randomly selected direction, which is accompanied by a change in the position of the lamination along the pipeline surface.

As described, the monitoring routine 9 shown in FIG. 3 particularly has two functions: On the one hand, it checks if the stop criterion is reached, on the other hand, it allocates the resources of the EDP unit between the individual experts based on their successes. A measure of success is $$P = \frac{\Delta F}{N},$$

wherein $\Delta F$ is the reduction of the fitness function F by the result of the respective expert routine, and in this case N is the number of simulations required for this. An assessment of the n expert routines can be assumed as $$R_n = \frac{P_n}{\Sigma P_i}.$$

The number of computation slots $N_S$ for an expert routine in one iteration then is $N_S = \text{int}(R_n N_{all})$, wherein $N_{all}$ is the number of all available slots.

The respective non-destructive measurements for the expert defect geometries are simulated in the simulation routines 16. An expert routine can iterate until it finds a solution whose expert prediction data sets are better than the initial prediction data sets stored in area 12. If this is the case, the expert routine 11 can attempt to achieve other better solutions on the basis of the already improved solution.

A resulting error E for the individual observations of the simulated and measured data sets can result from the errors of the respective data sets in the individual calculations:

$E = \Sigma_i \| Y_{cal}^i(D) - Y_m^i \|$, wherein $Y_m^i$ and $Y_{cal}^i$ represent the above-described respective measured and simulated measuring fields at the defect geometries $(x_1 \ldots x_n)$.

Figure 4A:
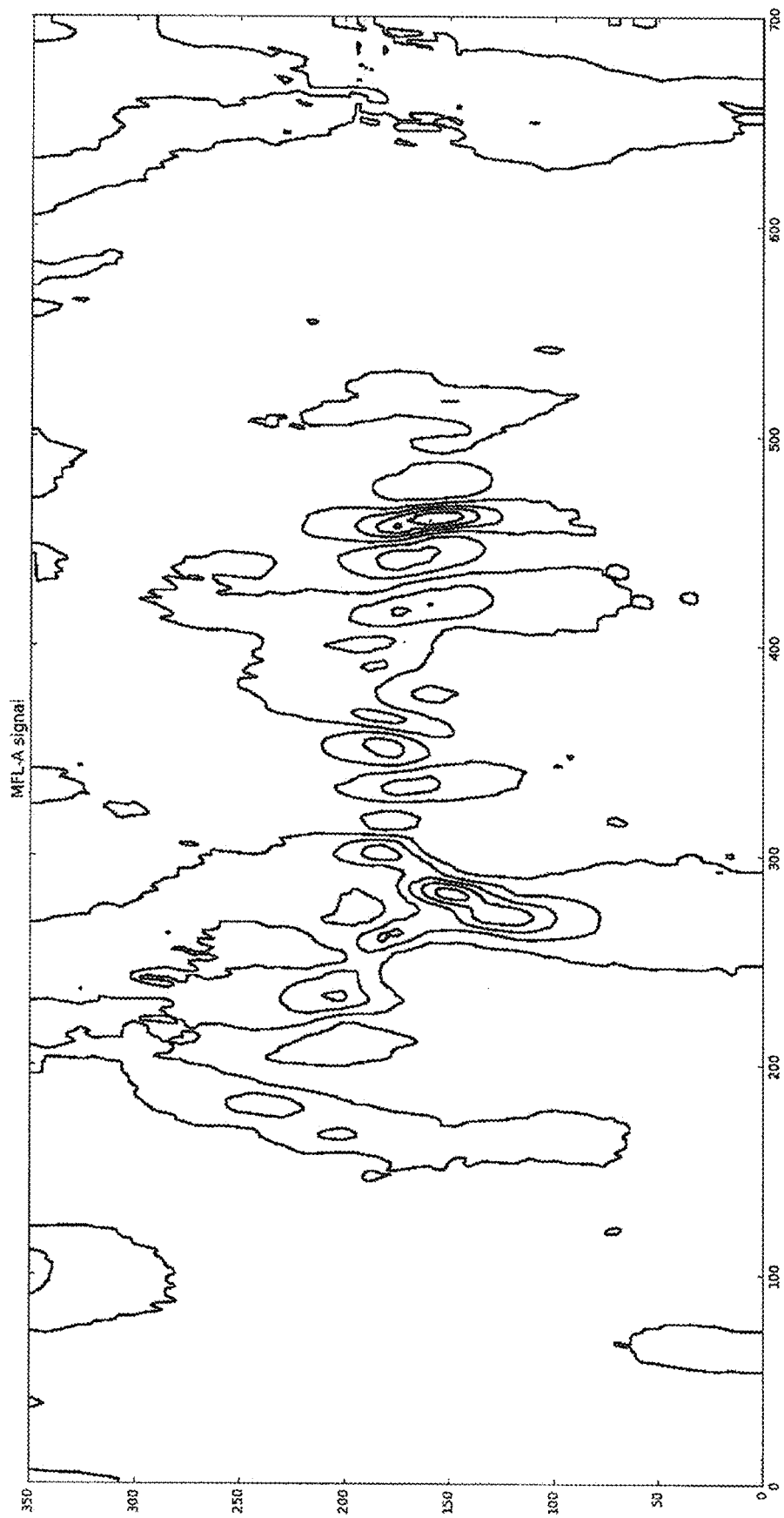
FIGS. 4A-4F show reference data sets and result of a method according to the invention in comparison with an associated geometry scan.
Figure 4B:
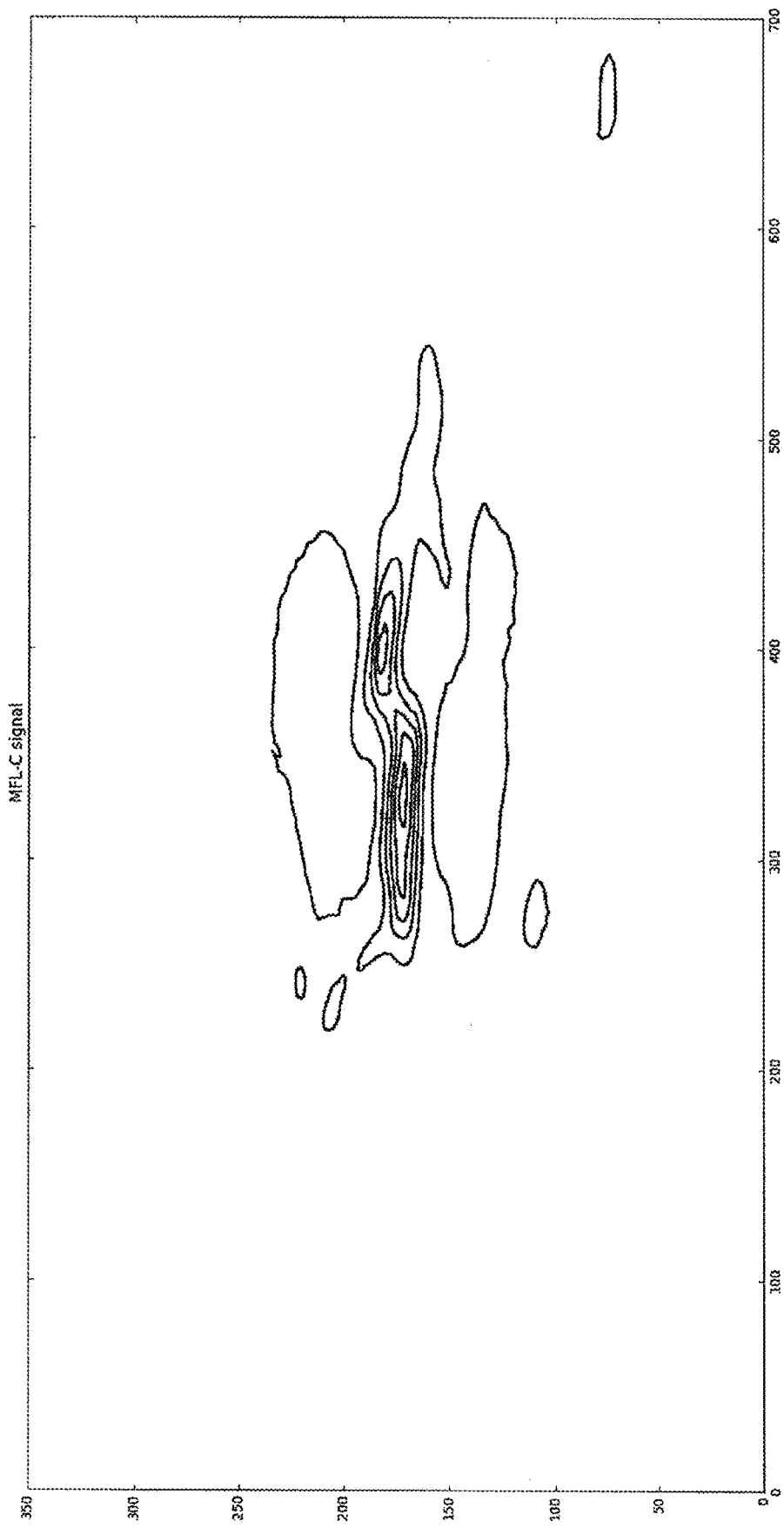
Figure 4C:
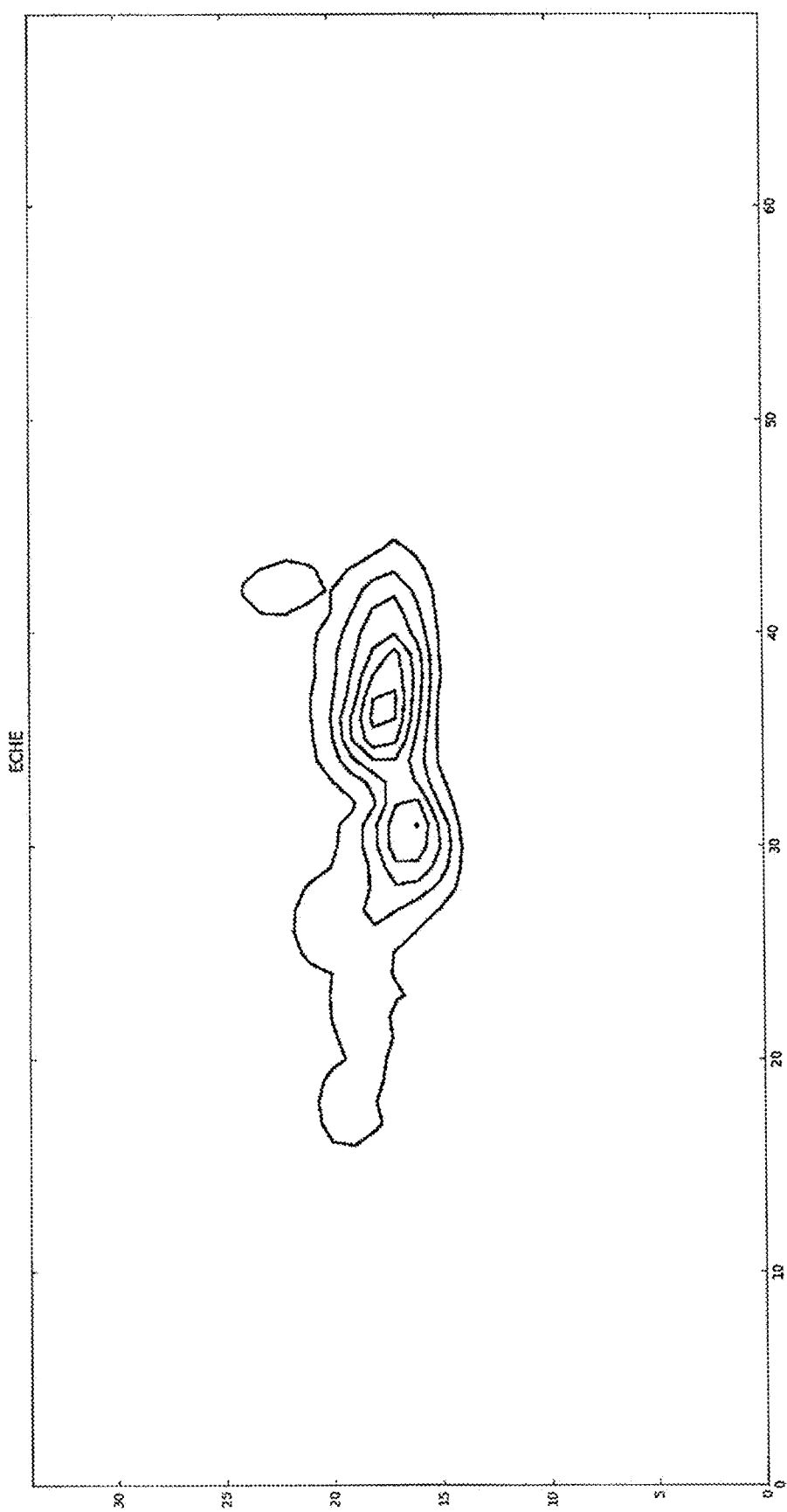
Figure 4D:
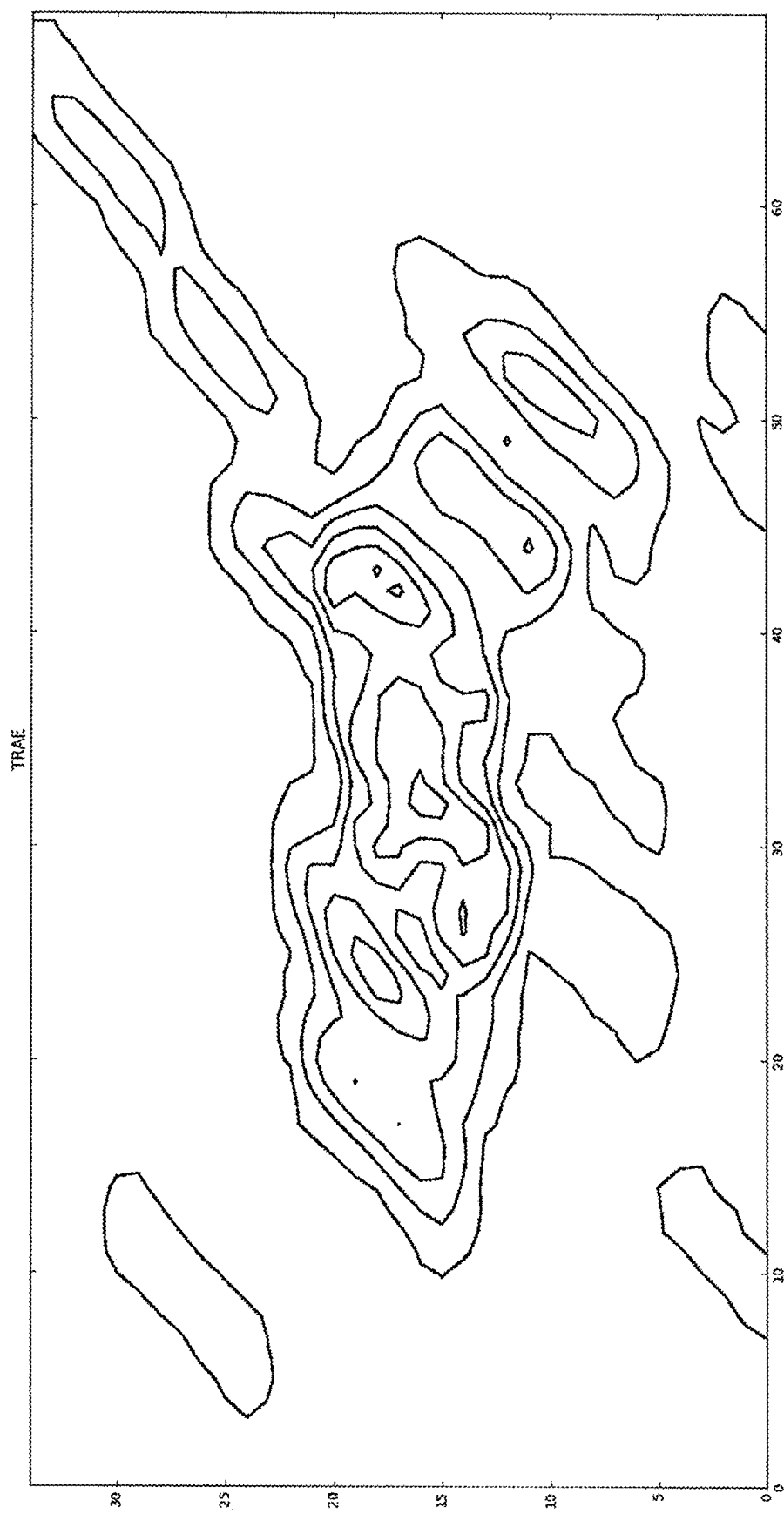

To demonstrate the efficiency of the proposed method, a large number of test scenarios were carried out, wherein the data of two MFL inspection runs that were carried out with magnetizations that are linearly independent of one another are used below, according to FIGS. 4A and 4B. FIG. 4A shows data from a real MFL measurement with magnetization running in the axial direction at a signal strength between 22.2 and 30.6 kA/m, while the data according to FIG. 4B resulted from a measurement in the circumferential direction (signal strength 22.2 to 91.1 kA/m). In both figures, the contour lines are evenly distributed over the specified area. In addition, two data sets obtained by an EMAT method are used as reference data sets, wherein the data set shown in FIG. 4C shows the received signal of a receiving transducer that detects reflections due to defects and the reference data set shown in FIG. 4D shows the associated transmission signal of a reference transducer. In each case, standardized signals are shown in the form of counts. After their preparation, which in the present case includes a series of Fourier transforms, both EMAT data sets are made available as input data for a neural network by means of a respective input layer. The two MFL data sets are also made available to the neural network via respective input layers.

Figure 4E:
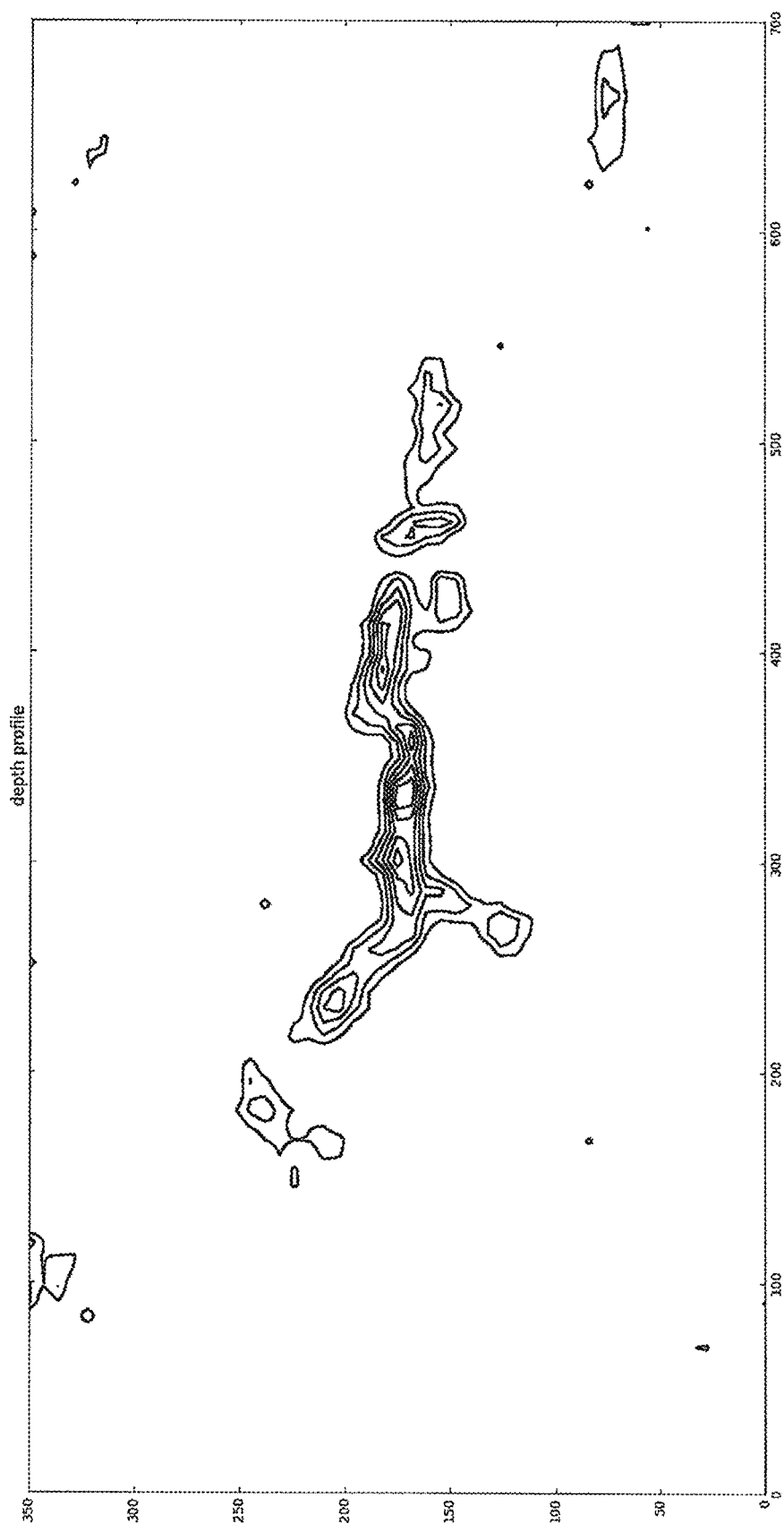
Figure 4F:
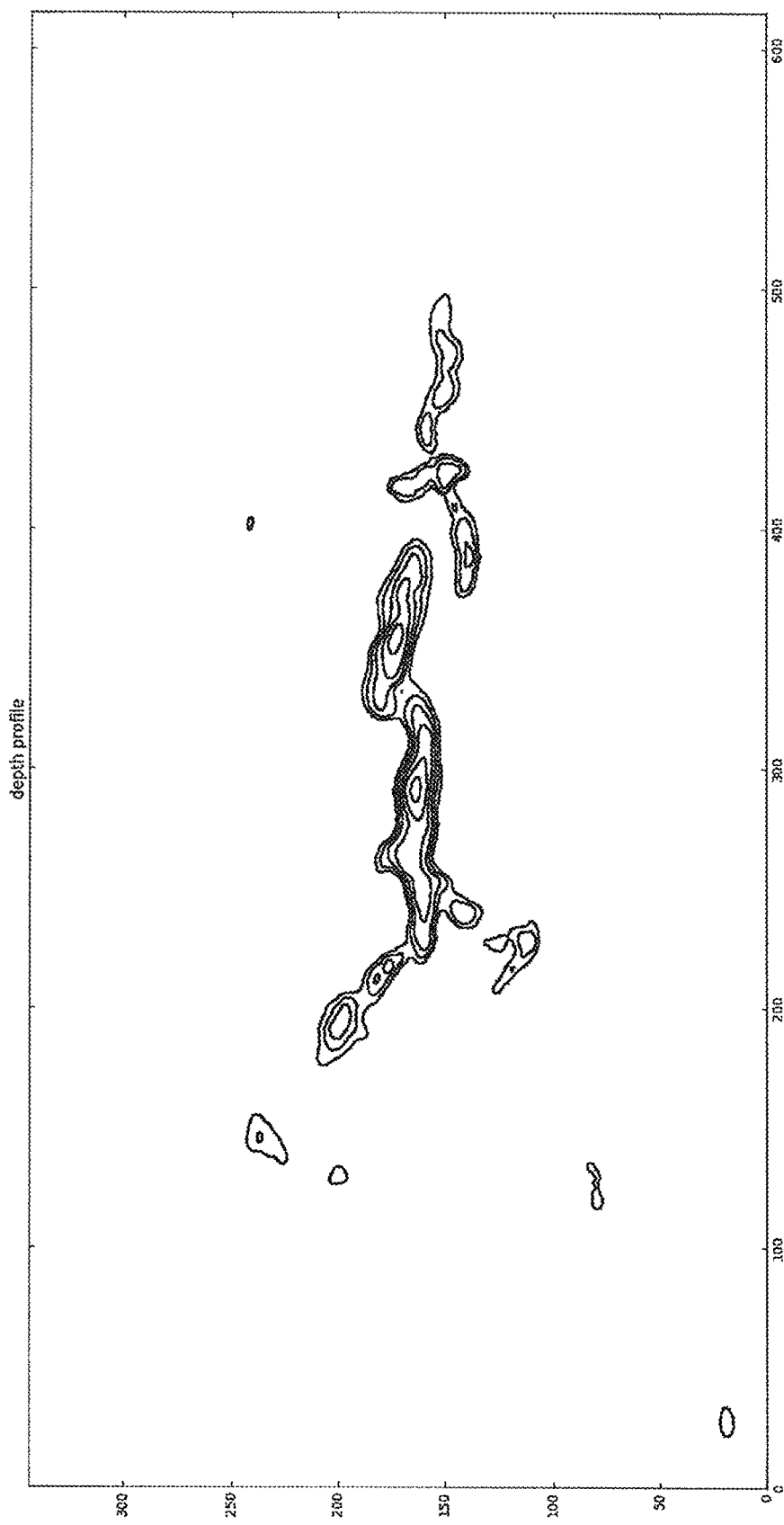

An initial defect geometry was determined on the EDP unit via the neural network, which geometry was then iteratively improved until a stop criterion was reached. The result of the method according to the invention is shown in FIG. 4E, which shows the depth of any defects on the inside of the pipeline section under review. Due to the method according to the invention, there is great agreement with the real geometry determined by a laser scan (FIG. 4F). Both in FIGS. 4E and 4F, a range of 0 to 60% metal loss of the pipe wall is outlined by means of the contour lines. The combination of the MFL and EMAT measurement data in the method according to the invention leads in the present case more quickly to a result than if only MFL data had been used, for example. The time saved is around 20%. At the same time, the combined consideration of the two different measuring methods shows that the presently detected defects are purely corrosion-based.

Figure 6:
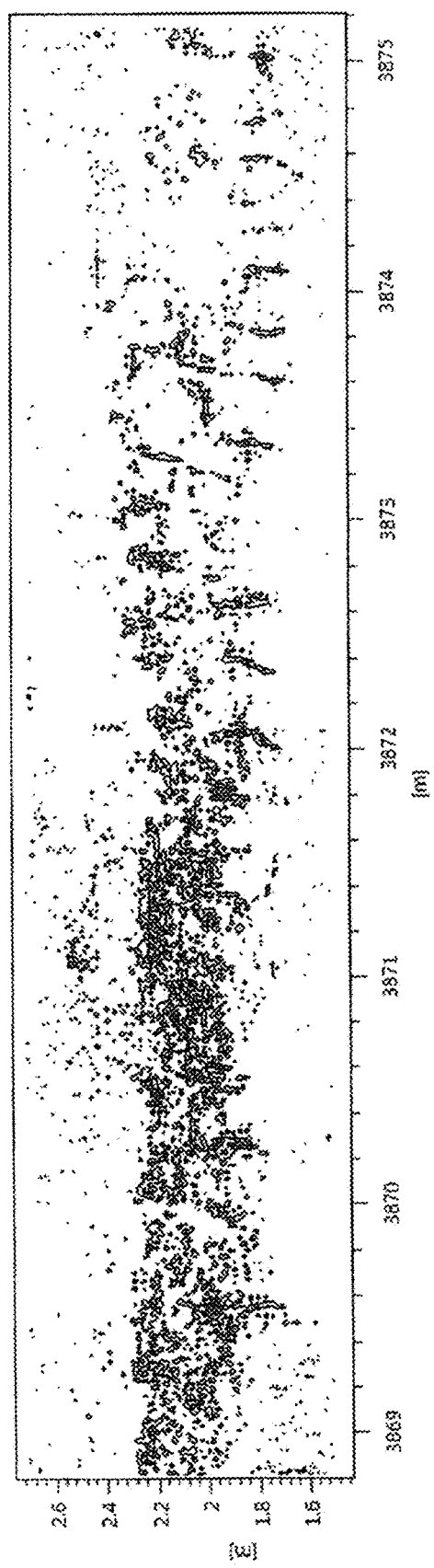
FIG. 6 shows the result of a method according to the invention.

The above-mentioned burst pressure of 4744.69 kPa results based on the conventional consideration with the determination of the defect geometry established in the prior art and shown in the result in FIG. 1. The defect geometry shown in FIG. 6 results (contour lines at 2 mm depth) and a burst pressure of 8543.46 kPa results based on the method according to the invention for the MFL and EMAT data sets on which FIG. 1 is also based. In the present case, this reaches up to 99.4% of the burst pressure, which was determined based on the actual defect geometry determined by laser scan. Accordingly, a pipeline examined using the method according to the invention can be operated at a safe operating pressure of 6520.53 kPa. This results in considerable advantages for pipeline operators compared to the safe operating pressure of 3621.29 kPa based on the evaluation according to the prior art (FIG. 1). As a result of the additional use of the EMAT reference data set, the result in the present case has neither worsened nor improved compared to the consideration of only the MFL data sets, since according to the method according to the invention there were no cracks and no lamination or laminating defects in the pipe section under review that would have negatively affected the consideration of the burst pressure.

Figure 7A:
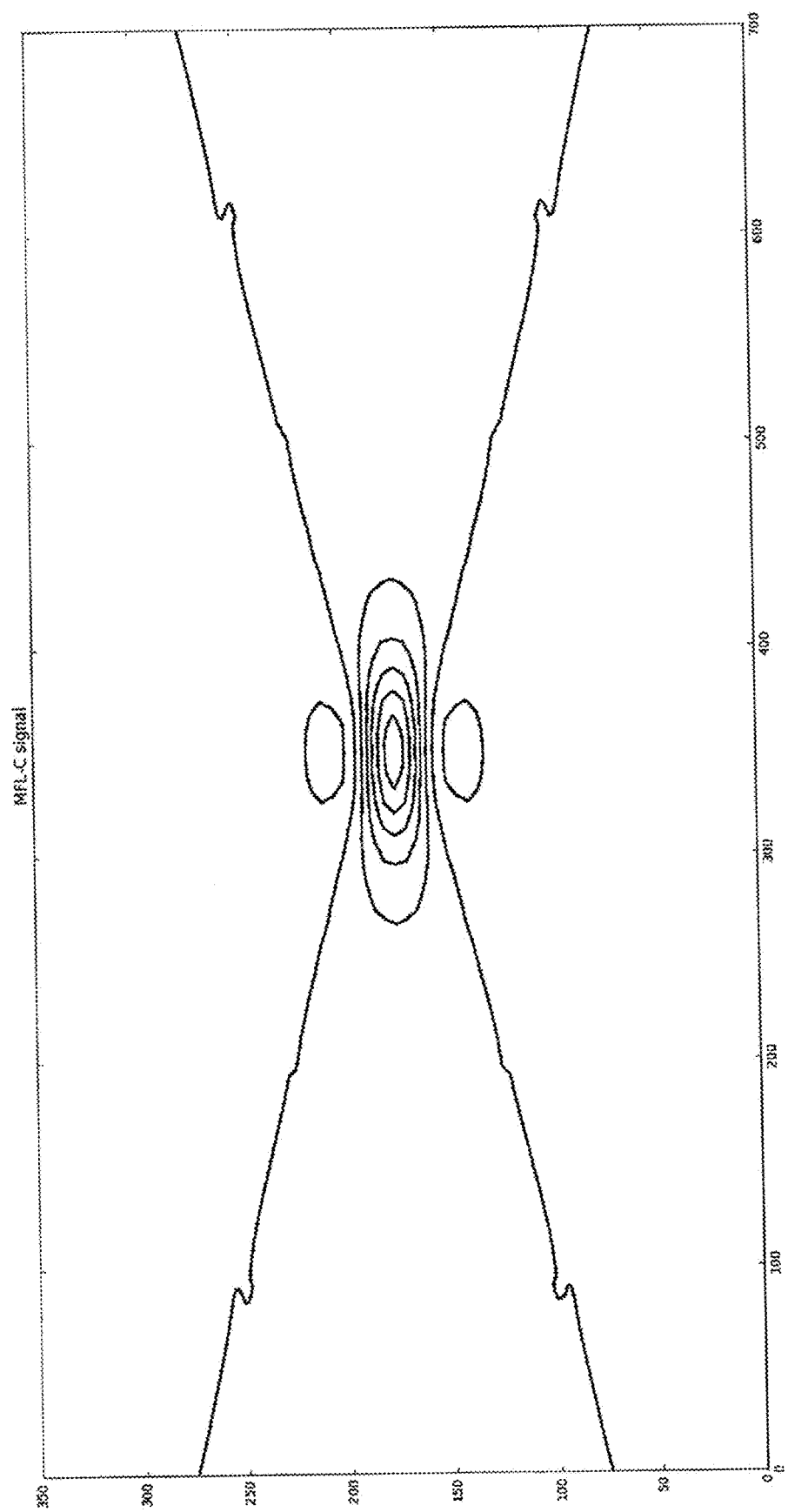
FIGS. 7A-7E show data sets and the result of a method according to the invention.
Figure 7B:
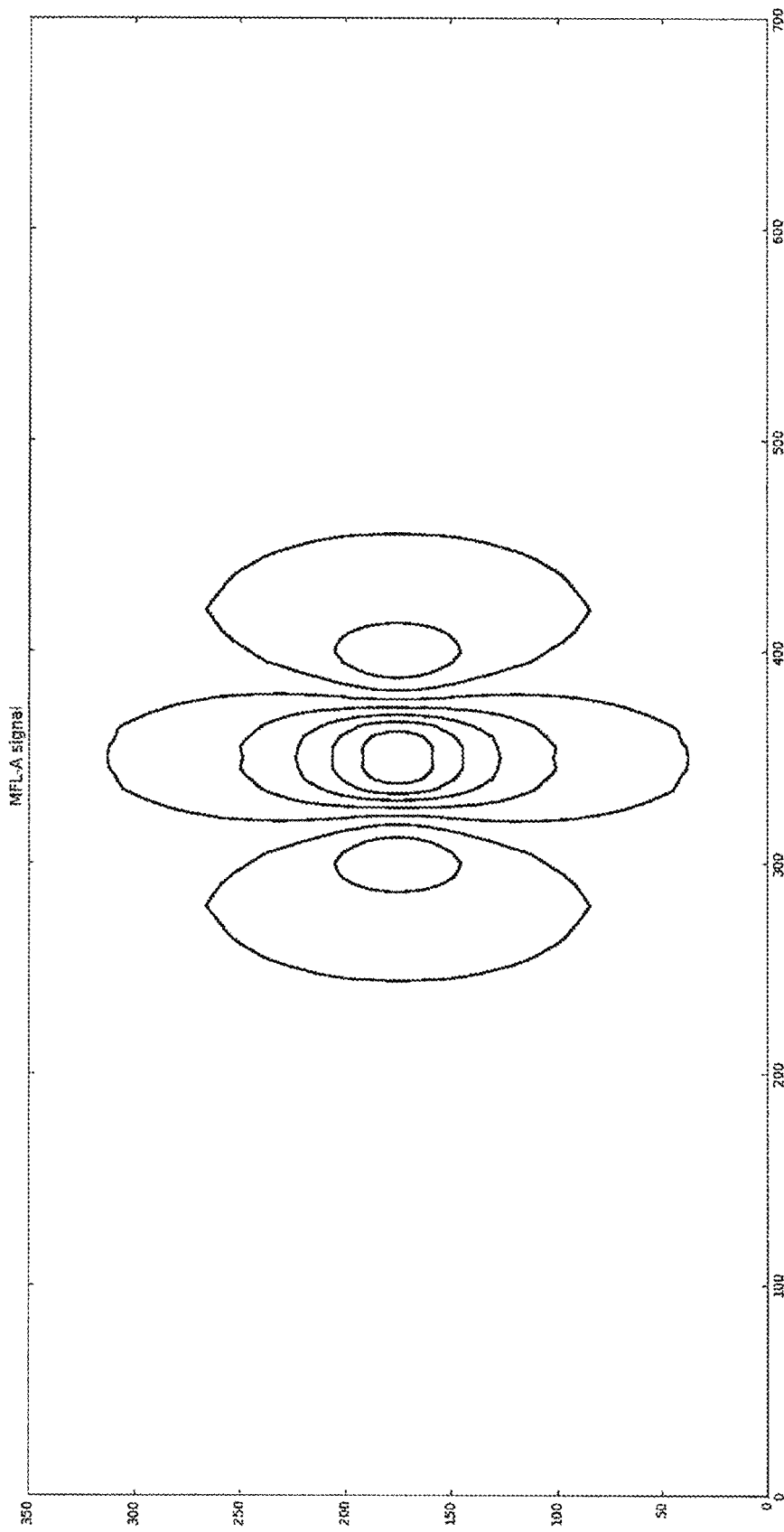
Figure 7C:
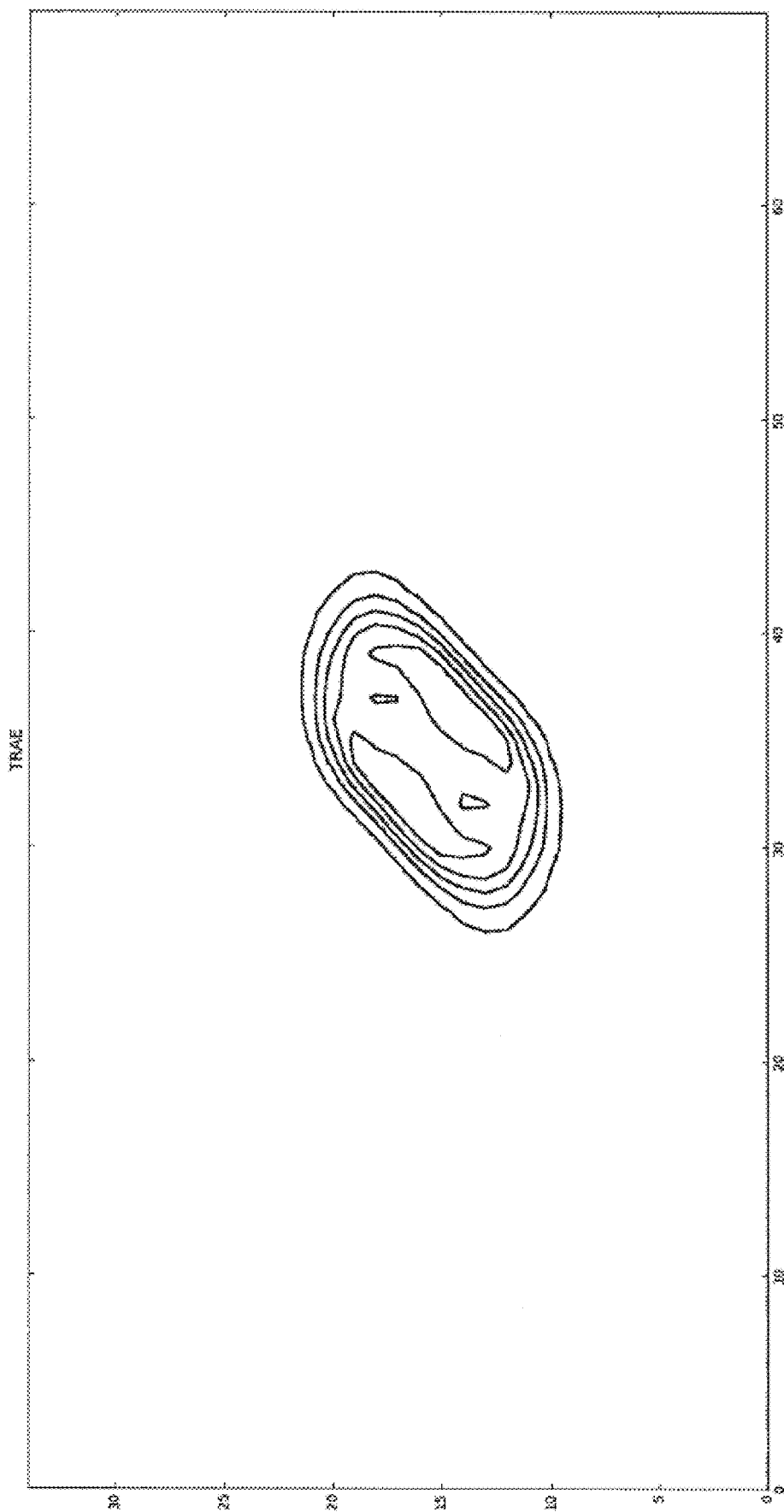
Figure 7D:
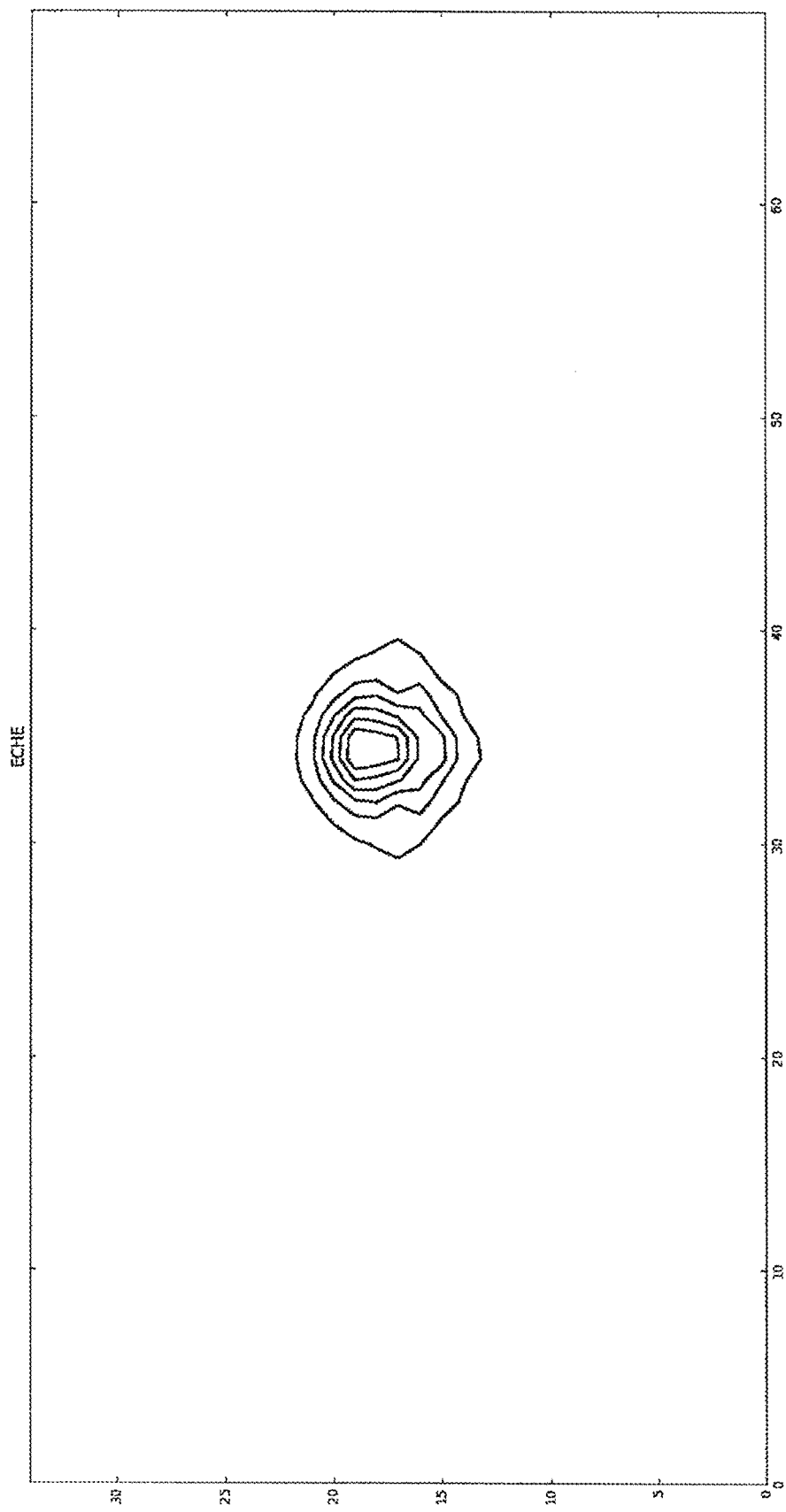
Figure 7E:
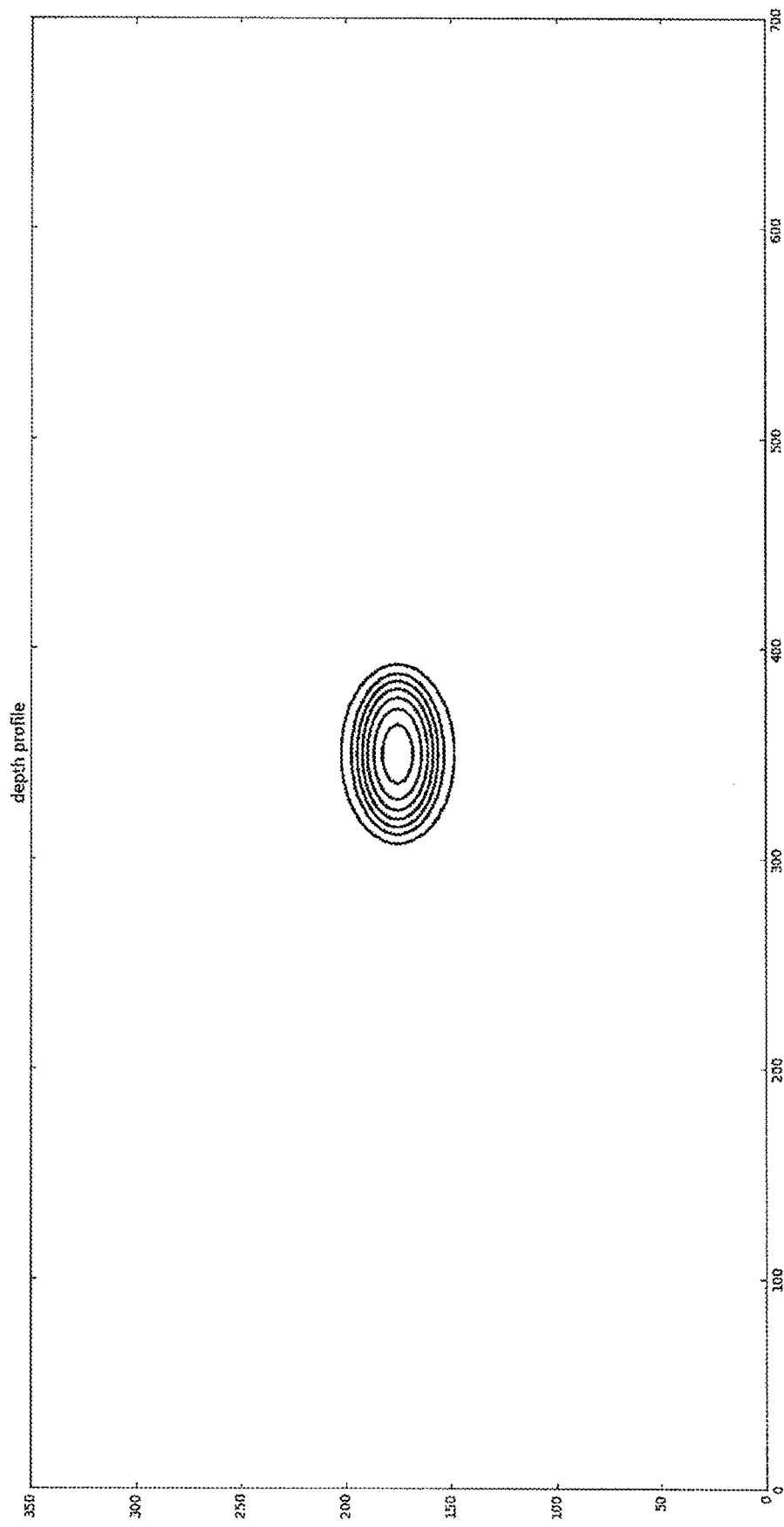

FIGS. 7A to 7E show by way of example the data sets used in another exemplary embodiment of a method according to the invention, this being an artificially created defect in a test tube. FIG. 7A shows an MFL signal (MFL-C signal) produced with a magnetization running in the circumferential direction of the examined pipeline section. The data set shown in FIG. 7B originates from another MFL measurement with magnetization linearly independent thereof in the axial direction. These two reference data sets are included in the evaluation together with a data set from an EMAT method. The transmission data shown in FIG. 7C and the echo data shown in FIG. 7D for a reference transducer or a receiving transducer belong to the EMAT method. The simple corrosion profile shown in FIG. 7E was found based on these two different non-destructive measuring methods. In the present case, this describes a simple defect purely due to corrosion.

Figure 8:
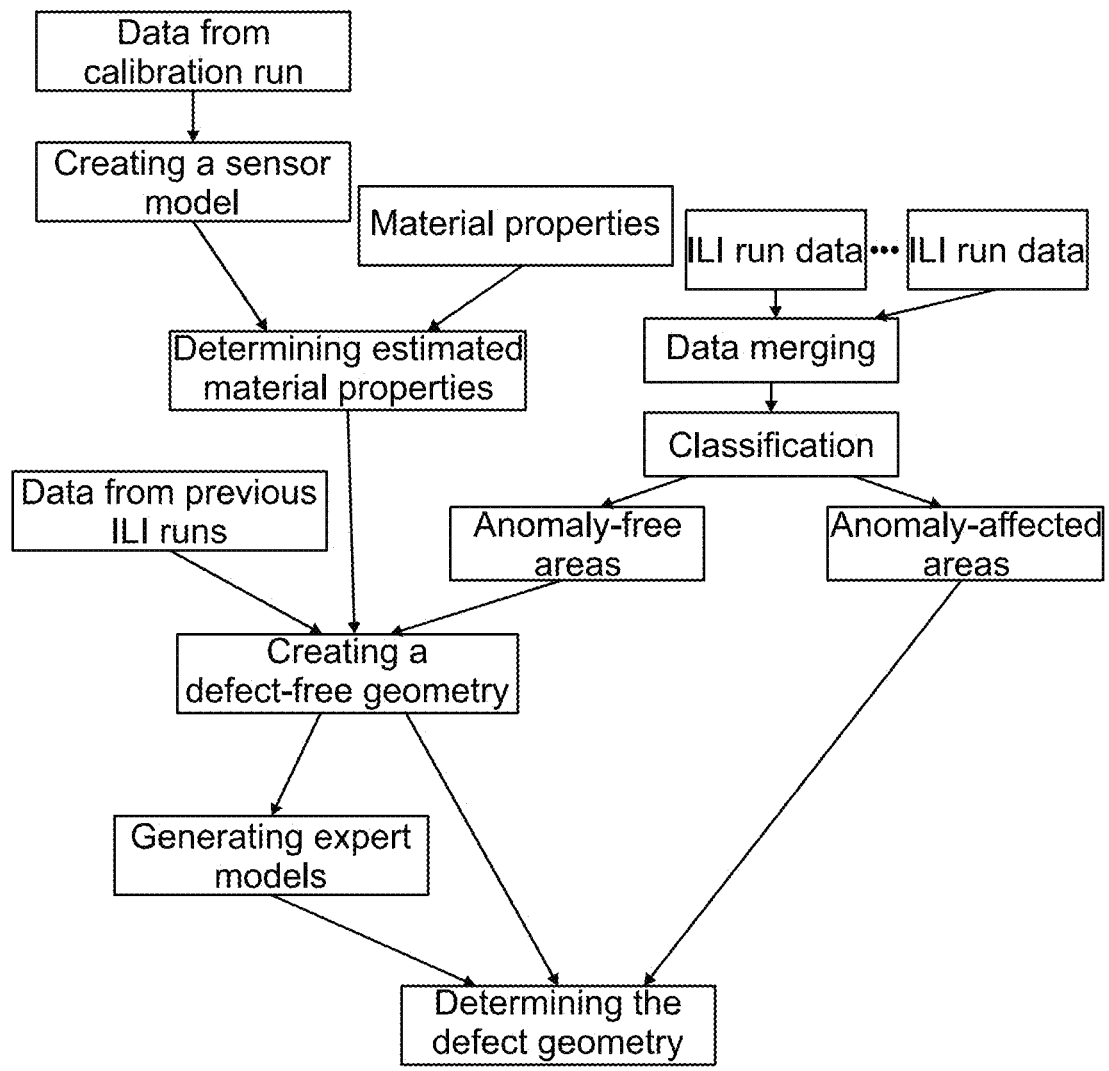
FIG. 8 shows a flow diagram of an exemplary embodiment of a method according to the invention.

FIG. 8 shows the flow chart of a possible implementation of the method according to the invention. A model for the non-destructive working sensor is created based on measurement data from one or more calibration measurements with a non-destructive measuring method on a calibration object of known geometry, particularly with defects of known geometry. A simulation routine is set up with an assessment of the relevant material properties of the examined object. This can be done by specifying known parameters that represent the material properties and properties of the sensor used. Alternatively or additionally, the parameters can be iteratively adjusted until the results of the simulation routine for the non-destructive measuring method used, based on the known geometry of the calibration object, match the measurement data of the calibration measurement with sufficient accuracy. The simulation routine can also be prepared and reused for multiple measurements using the non-destructive measuring method.

One or more reference data sets are created on based on one or more measurements with one or more non-destructive measuring methods. FIG. 8 shows the creation of a reference data set based on multiple measurement runs. A classification into anomaly-free areas and anomaly-afflicted areas is carried out based on the reference data set. By using two or more reference data sets that were obtained based on different non-destructive measuring methods, the classification can be improved again in such a way that individual measuring methods are more sensitive to specific defects than to others.

An object grid representing the intact geometry of the object is created based on the anomaly-free areas and using the simulation routine. For this purpose, information from previous measurement runs in the object with no or fewer defects can also be used. For this purpose, the object grid can be created in the anomaly-free areas and then completed by extrapolating and/or interpolating into the anomaly-afflicted areas. It is also conceivable to carry out an interpolation and/or extrapolation based on the reference data sets from the anomaly-free areas into the anomaly-afflicted areas.

The object grid is created using an iterative process. A first initial object grid is guessed, estimated or, for example, specified based on an estimated object geometry. This is adjusted in an iterative process. An initial object grid can, for example, have a weld seam according to the one shown in cross section in FIG. 9. The initial grid can be iteratively adjusted until it has a shape that represents the weld seam.

Figure 9:
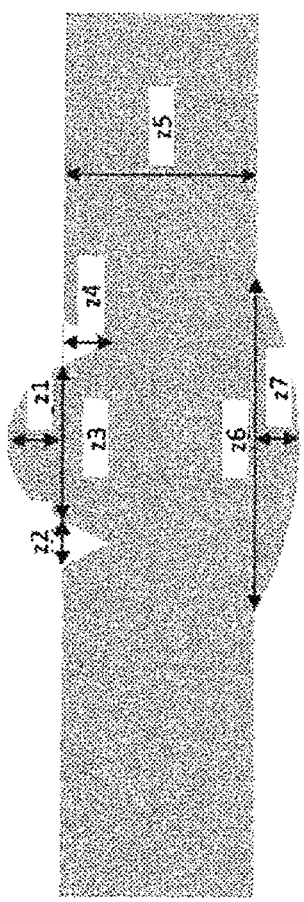
FIG. 9 shows an illustration of a parameter representation of a weld.

A parametric description of the weld seam by means of a parametric geometry model can in particular also be used to accelerate the method. FIG. 9 shows such a parametric geometry model. In this model, the shape of the weld seam is described by a small number of parameters, in this case seven. The parameters describe the wall thickness of the object ($z_5$), the respective extension of the weld seam on both sides ($z_3$, $z_6$), the weld seam elevation ($z_1$, $z_7$), as well as the width and depth of notches on the weld seam ($z_2$, $z_4$). The object grid can thus be changed in the area of the weld seam by adjusting a small number of parameters. In this case, previously known information about a general shape of an object area, here a weld seam, is used. Additional boundary conditions can be specified for individual parameters. This rules out physically nonsensical or impossible results. In FIG. 9, for example, the parameters $z_2$, $z_3$, $z_5$ and $z_6$ cannot reasonably be negative, $z_4$ cannot reasonably be greater than $z_5$, etc. The parameter values can be determined by the following optimization problem:

$$\{z_1 \ldots z_n\} = \operatorname*{argmin}_i \sum |Y_{cal}^i(z_1 \ldots z_n) - Y_m^i| \text{ under boundary conditions for} \{z_1 \ldots z_n\}$$

wherein $Y_m^i$—is the measured signal of the i-th measurement, $Y_{cal}^i$ is the calculated signal for the i-th measurement. Values for the parameters can be determined using derivative-free optimization algorithms, for example by means of random search. The parameters can be changed in fixed steps, preferably defined as a function of the wall thickness, to accelerate the method. For example, a change can be made in steps that are 1% of the wall thickness.

Based on the method according to the invention, the condition of a pipe and thus the pressure that can be specified for safe operation of the pipeline can be specified much more realistically, while operational reliability is still ensured. Such a result can be made available to the pipeline operators more quickly than in the prior art using the method according to the invention with the expert routines competing for resources of the EDP unit.

The invention claimed is:

1. A method for determining the geometry of one or more real, examined defects of a metallic pipeline by at least two reference data sets of the object generated based on different, non-destructive measuring methods, the object being displayed at least partially on or through a single at least two-dimensional object grid in an EDP unit, the method comprising the steps of:
sensing the defects of the metallic pipeline, while the pipeline is under pressure, with at least two different sensors of different types, each sensor implementing a different measurement operation and transmitting a respective reference data set;
determining at least one starting defect geometry as an initial defect geometry based on previous information on the metallic pipeline;
determining respective prediction data sets as initial prediction data sets based on the initial defect geometry by simulation or assignment of a measurement that matches the respective reference data sets;
iteratively adjusting the initial defect geometry to the geometry of the one or more real, examined defects by the EDP unit and by at least one particularly competing expert routine;
generating a respective expert defect geometry in a respective at least one expert routine by at least one separate algorithm and based on the initial defect geometry;
determining respective expert prediction data sets based on the respective expert defect geometry by simulation or assignment of a measurement that matches the respective reference data sets;
making available the expert defect geometry, on which the respective expert prediction data sets are based, the respective at least one expert routine as a new initial defect geometry for further adjustment to the geometry of the one or more real, examined defects;
when the expert prediction data sets of the respective expert routine are more similar to the respective reference data sets than the initial prediction data sets and/or a fitness function that takes into account the at least two expert prediction data sets is improved, the expert prediction data sets belonging to the new initial defect geometry are used as new initial prediction data sets,
wherein the iterative adjustment by means of the at least one expert routine takes place until a stop criterion is met;
calculating a load limit of the metallic pipeline using the expert defect geometry that met the stop criterion, the load limit being a burst pressure of the pipeline; and
operating the pipeline at an operating pressure below the burst pressure, based on the calculated burst pressure.

2. The method according to claim 1, wherein a data set based on an MFL, eddy current, EMAT, or ultrasonic measuring method is used as the first reference data set and a data set generated based on another and different of said measuring methods is used as the other reference data set.

3. The method according to claim 1, wherein the initial defect geometry is determined on the object grid, an at least two-dimensional defect grid and/or via a parameter representation.

4. The method according to claim 1, wherein at least one simulation parameter obtained from a calibration run of the inspection device belonging to the measuring method and/or at least one material-specific parameter of the pipeline are used for the measuring method-specific generation of the initial and/or expert prediction data sets.

5. The method according to claim 1, wherein the at least one expert routines run in competition with one another in such a way that the resources of the EDP unit to a respective expert routine are distributed as a function of a success rate.

6. The method according to claim 1, wherein initial and/or expert prediction data sets are generated on the basis of a forward model for simulating the respective non-destructive measuring method.

7. The method according to claim 1, wherein the starting defect geometry is generated by means of a look-up table, by one of the expert routines, and/or by a machine learning algorithm.

8. The method according to claim 7, wherein the starting defect geometry is generated by inversion of at least parts of the reference data sets using at least one neural network trained for this task.

9. The method according to claim 1, wherein, to determine the object grid, anomaly-free areas and anomaly-afflicted areas of the pipeline are first classified on the basis of at least parts of the reference data sets, wherein an initial object grid is created particularly on the basis of previously known information about the pipeline, the initial object grid is used to calculate prediction data sets for the respective non-destructive measuring methods, at least parts of the prediction data sets are compared with respective parts of the reference data sets while excluding the anomaly-afflicted areas, and, depending on at least one degree of accuracy, either the initial object grid is used as the object grid describing the geometry of the pipeline or an iterative adjustment of the initial object grid to the geometry of the pipeline in the anomaly-free areas is carried out by means of the EDP unit.

10. The method according to claim 9, wherein, in the iterative adjustment of the initial object grid, a new initial object grid is created and new prediction data sets are calculated for it, and at least parts of the new prediction data sets are compared to corresponding parts of the reference data sets, excluding the anomaly-afflicted areas until an object stop criterion is met, and the initial object grid then present is used as the object grid describing the geometry of the pipeline.

11. The method according to claim 9, wherein an anomaly-free area is assigned to at least one predefined local element of the pipeline during the classification and this element is used in the creation of the initial object grid or inserted into the initial object grid.

12. The method according to claim 11, wherein the local element is described by means of a parametric geometry model.

13. The method according to claim 1, wherein the initial defect geometry or a pointer referring thereto is stored in a memory area of the EDP unit that is accessible to all expert routines.

14. The method according to claim 1, wherein the stop criterion is assumed to be a substantial change in the initial defect geometry, in the geometry of the object pipeline and/or defect grid, in the initial prediction data set and/or in at least one expert prediction data set, which change does not occur after a plurality of iterations.

15. The method according to claim 1, wherein a comparison of the variation of the expert prediction data set to the measurement spread of the real data set is used as the stop criterion.

16. The method according to claim 1, wherein an expert routine is assigned one or more algorithms for generating and/or adjusting the expert defect geometry including machine learning, stochastic optimization, empirical and/or numerical model functions.

17. The method according to claim 16, wherein an algorithm is generated randomly in an expert routine or is selected and/or changed by a selection function.

18. The method according to claim 1, wherein different and defect-specific variations for generating the expert defect geometry are carried out in each expert routine.

19. The method according to claim 18, wherein, in the expert routines, a parameter representation of a respective defect, derived from or assigned to the initial defect geometry, is varied to generate the expert defect geometry.

20. The method according to claim 19, wherein a defect classification algorithm imaged preferably using a neural network classifies the defects of the initial defect geometry.

21. A method for determining a load limit of a pipeline that is under pressure at least during operation, wherein a data set describing one or more defects is used as an input data set in a calculation of the load limit, and wherein the input data set is generated first according to a method according to claim 1.

* * * * *

UNITED STATES PATENT AND TRADEMARK OFFICE
CERTIFICATE OF CORRECTION

| | | |
|---|---|---|
| PATENT NO. | : 12,359,913 B2 | Page 1 of 1 |
| APPLICATION NO. | : 17/602939 | |
| DATED | : July 15, 2025 | |
| INVENTOR(S) | : Andrey Danilov and Matthias Peussner | |

It is certified that error appears in the above-identified patent and that said Letters Patent is hereby corrected as shown below:

In the Claims

Claim 14, Column 26, Line 7, before the term "pipeline" delete "object"

Signed and Sealed this
Eighteenth Day of November, 2025

John A. Squires
*Director of the United States Patent and Trademark Office*